(12) United States Patent
Kong et al.

(10) Patent No.: US 11,878,987 B2
(45) Date of Patent: Jan. 23, 2024

(54) HETEROCYCLIC COMPOUND AS TRK INHIBITOR

(71) Applicant: Beijing Innocare Pharma Tech Co., Ltd., Beijing (CN)

(72) Inventors: Norman Xianglong Kong, Nanjing (CN); Chao Zhou, Nanjing (CN); Zhixiang Zheng, Nanjing (CN)

(73) Assignee: Beijing Innocare Pharma Tech Co., Ltd., Beijing (CN)

( * ) Notice: Subject to any disclaimer, the term of this patent is extended or adjusted under 35 U.S.C. 154(b) by 611 days.

(21) Appl. No.: 17/255,797

(22) PCT Filed: Jun. 25, 2019

(86) PCT No.: PCT/CN2019/092653
§ 371 (c)(1),
(2) Date: Dec. 23, 2020

(87) PCT Pub. No.: WO2020/001415
PCT Pub. Date: Jan. 2, 2020

(65) Prior Publication Data
US 2021/0147445 A1 May 20, 2021

(30) Foreign Application Priority Data
Jun. 25, 2018 (CN) .......................... 201810660162.6

(51) Int. Cl.
C07D 498/22 (2006.01)

(52) U.S. Cl.
CPC .................................. *C07D 498/22* (2013.01)

(58) Field of Classification Search
CPC .................................................... C07D 498/22
See application file for complete search history.

(56) References Cited

U.S. PATENT DOCUMENTS

| | | | |
|---|---|---|---|
| 8,933,084 B2 * | 1/2015 | Andrews | A61P 33/02 |
| | | | 544/242 |
| 9,447,104 B2 | 9/2016 | Haas et al. | |
| 9,493,476 B2 * | 11/2016 | Andrews | A61P 31/04 |
| 9,676,783 B2 | 6/2017 | Haas et al. | |
| 9,718,822 B2 | 8/2017 | Andrews et al. | |
| 9,750,744 B2 | 9/2017 | Andrews et al. | |
| 9,840,519 B2 | 12/2017 | Andrews et al. | |
| 9,902,741 B2 | 2/2018 | Andrews et al. | |
| 2013/0203776 A1 | 8/2013 | Andrews et al. | |
| 2015/0005499 A1 | 1/2015 | Haas et al. | |
| 2015/0336970 A1 | 11/2015 | Andrews et al. | |
| 2016/0228441 A1 * | 8/2016 | Haas | A61K 31/519 |
| 2017/0107232 A1 | 4/2017 | Andrews et al. | |
| 2017/0283435 A1 | 10/2017 | Andrews et al. | |
| 2018/0127427 A1 | 5/2018 | Haas et al. | |
| 2019/0031684 A1 | 1/2019 | Andrews et al. | |
| 2019/0211017 A1 | 7/2019 | Haas et al. | |
| 2021/0147445 A1 | 5/2021 | Kong et al. | |

FOREIGN PATENT DOCUMENTS

| | | |
|---|---|---|
| CN | 102971322 A | 3/2013 |
| CN | 103509017 A | 1/2014 |
| CN | 105693720 A | 6/2016 |
| CN | 110156813 A | 8/2019 |
| EP | 3822276 A1 | 5/2021 |
| WO | WO-2011/006074 A1 | 1/2011 |
| WO | WO-2011/146336 A1 | 11/2011 |
| WO | WO-2013/046029 A1 | 4/2013 |
| WO | WO-2015/112806 A2 | 7/2015 |
| WO | WO-2017/075107 A1 | 5/2017 |
| WO | WO-2019/094143 A1 | 5/2019 |
| WO | WO-2019/149131 A1 | 8/2019 |
| WO | WO-2019/157879 A1 | 8/2019 |
| WO | WO-2019/201131 A1 | 10/2019 |
| WO | WO-2020001415 A1 | 1/2020 |

OTHER PUBLICATIONS

Extended European Search Report for EP Application No. 198257164 dated Mar. 3, 2022.
Brodeur et al., "Trk Receptor Expression and Inhibition in Neuroblastomas," Clin Cancer Res., 15(10): 3244-3250 (2009).
Khotskaya et al., "Targeting TRK family proteins in cancer," Pharmacology & Therapeutics, 173: 58-66 (2017).
Russo et al., "Acquired Resistance to the TRK Inhibitor Entrectinib in Colorectal Cancer," Cancer Disco., 6(1): 36-44 (2016).
Vaishnavi et al., "TRKing down an old oncogene in a new era of targeted therapy," Cancer Disco., 5(1): 25-34 (2015).
International Search Report for International Application No. PCT/CN2019/092653 dated Sep. 30, 2019.

* cited by examiner

*Primary Examiner* — Timothy R Rozof
(74) *Attorney, Agent, or Firm* — Foley Hoag LLP; Dana M. Gordon; Oluyinka Green

(57) ABSTRACT

The present invention relates to a compound, a pharmaceutical composition comprising the compound, the method for the preparation thereof, and the use thereof as TRK inhibitors. The compound is a compound as shown in the following formula I, and isomers, prodrugs, solvates, stable isotopic derivatives or pharmaceutically acceptable salts thereof. The present invention also relates to use of the compound in treating or preventing diseases mediated by TRK, such as cancers, and method for treating such diseases using the compounds of the present invention.

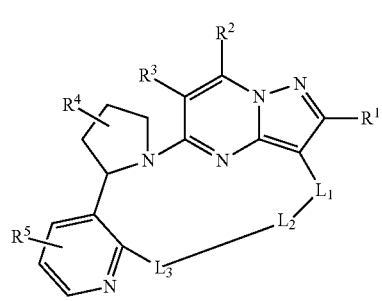

I

10 Claims, No Drawings

HETEROCYCLIC COMPOUND AS TRK INHIBITOR

RELATED APPLICATIONS

This application is the U.S. national phase of International Patent Application No. PCT/CN2019/092653, filed Jun. 25, 2019; which claims the benefit of priority to Chinese Application No. 201810660162.6, filed Jun. 25, 2018.

TECHNICAL FIELD

The present invention relates to compounds, pharmaceutical compositions containing thereof, and their use as TRK inhibitors. More specifically, the present invention provides new compounds as TRK inhibitors, pharmaceutical compositions containing such compounds, and methods of applying the compounds to treat or prevent TRK mediated diseases, such as tumors. The invention also relates to methods for preparing compounds as described below.

BACKGROUND ART

TRK (tropomyosin receptor kinase) is a tyrosine kinase of neurotrophic receptor presented in many tissues, and it activates a variety of downstream processes in cell proliferation and survival. There are three members in the TRK proto-oncogene family: TRK A, B and C, which are encoded by NTRK1, NTRK2 and NTRK3 respectively. The binding of neurotrophic factors and TRK proteins leads to receptor dimerization, phosphorylation and activation of downstream signaling pathways such as Ras/MAPK, PI3K/Akt and PLC γ pathways, which regulate cell proliferation, differentiation, metabolism and apoptosis (Brodeur G. M., Minturn J. e., Ho R, et al. *Clinical cancer research*, 2009, 15, 3244-50). Genomic analysis of kinase fusion confirmed that NTRK gene fusion occurs in a variety of cancers, such as glioma, hepatobiliary carcinoma, papillary thyroid carcinoma, colon cancer, non-small cell lung cancer, head and neck squamous cell carcinoma, pancreatic cancer, sarcoma and melanoma (Khotskaya, Y. B. et al. *Pharmacology & Therapeutics*, 2017, 173, 58-66). TRK inhibitors can be used to treat various tumors caused by NTRK fusion protein, the research and development of TRK inhibitors is of great potential and broad market prospects. In the early clinical trials of TRK inhibitor larotrectinib (loxo-101), 38 patients (76%) achieved objective responses, and 6 patients (12%) were in complete remission and no tumor could be detected by existing methods. Of these patients, 30 patients had been in remission for more than a year (American Society of Clinical Oncology annual meeting 2017). However, the target mutation due to continuous drug administration leads to drug resistance. Cases with NTRK mutations have been found clinically, such as NTRK1 G595R and G667C mutations (Russo, M. et al., *Cancer discovery*, 2016, 6 (1), 36-44). Therefore, it is necessary to develop more active TRK inhibitors with fewer side effects and are still effective for TRK mutations.

SUMMARY OF THE INVENTION

The purpose of the present invention is to provide a compound as shown in formula I, and the isomers, prodrugs, solvates, stable isotopic derivatives or pharmaceutically acceptable salts thereof, which can be used as TRK inhibitors:

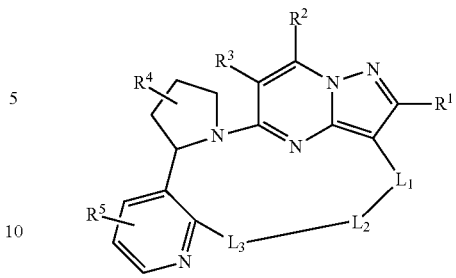

I Wherein:

$L_1$ is selected from —$NR^6C(O)$—, —$NR^6CON(R^7)$—, —$NR^6S(O)_m$— and —$NR^6S(O)_mN(R^7)$—, of which $NR^6$ is connected with the nitrogen-containing heteroaryl substituted by $R^1$, $R^2$, $R^3$; preferably, $L_1$ is selected from —$NR^6C(O)$— and —$NR^6CON(R^7)$—, of which $NR^6$ is connected with the nitrogen-containing heteroaryl substituted by $R^1$, $R^2$, $R^3$; most preferably, $L_1$ is selected from $NR^6CON(R^7)$—, of which $NR^6$ is connected with the nitrogen-containing heteroaryl substituted by $R^1$, $R^2$, $R^3$;

$L_2$ is selected from C1-C8 alkylene, C2-C8 alkenylene, C2-C8 alkynylene and C3-C8 cyclylene, wherein the alkylene, alkenylene, alkynylene and cyclylene can be optionally substituted by one or more G1; preferably, $L_2$ is selected from C1-C6 alkylene and C2-C6 alkenylene which can be optionally substituted by one or more G1; more preferably, $L_2$ is selected from C1-C4 alkylene which can be optionally substituted by one or more G1;

$L_3$ is selected from a single bond, —O— and —$N(R^x)$—; preferably, $L_3$ is selected from a single bond and —O—; most preferably, $L_3$ is —O—;

$R^1$, $R^2$, $R^3$ are each independently selected from hydrogen, halogen, cyano, C1-C8 alkyl, C3-C8 cyclyl, 3-8 membered heterocyclyl, aryl, heteroaryl, formyl, —$NR^8R^9$, —$C(O)R^{10}$, carboxyl, alkenyl, alkynyl, —$OR^{10}$, —$OC(O)NR^8R^9$, —$C(O)OR^{10}$, —$C(O)NR^8R^9$, —$NR^{11}C(O)R^{10}$, —$NR^{11}C(O)NR^8R^9$, —$S(O)mR^{10}$, —$NR^{11}S(O)mR^{10}$, —$SR^{10}$, —$S(O)mNR^8R^9$ and —$NR^{11}S(O)mNR^8R^9$, wherein the alkyl, cyclyl, heterocyclyl, aryl or heteroaryl are optionally substituted by one or more substituents selected from halogen, cyano, C1-C8 alkyl, C3-C8 cyclyl, 3-8 membered heterocyclyl, —$OR^{12}$, —$NR^{13}R^{14}$, —$OC(O)NR^{13}R^{14}$, —$C(O)OR^{12}$, —$C(O)R^{12}$, —$C(O)NR^{13}R^{14}$, —$NR^{15}C(O)R^{12}$, —$NR^{15}C(O)NR^{13}R^{14}$, —$S(O)mR^{12}$, —$NR^{15}S(O)mR^{12}$, —$SR^{12}$, —$S(O)mNR^{13}R^{14}$ and —$NR^{15}S(O)mNR^{13}R^{14}$; preferably, both $R^2$ and $R^3$ are hydrogen; more preferably, $R^1$, $R^2$, $R^3$ are all hydrogen;

$R^4$ is selected from hydrogen, halogen, cyano, C1-C8 alkyl, C3-C8 cyclyl, 3-8 membered heterocyclyl, aryl, heteroaryl, formyl, —$C(O)R^{10}$, carboxyl, alkenyl, alkynyl, —$OR^{10}$, —$NR^8R^9$, —$OC(O)NR^8R^9$, —$C(O)OR^{10}$, —$C(O)NR^8R^9$, —$NR^8C(O)R^{10}$, —$NR^{10}C(O)NR^8R^9$, —$S(O)mR^{10}$, —$NR^8S(O)mR^{10}$, —$SR^{10}$, —$S(O)mNR^8R^9$ and —$NR^{10}S(O)mNR^8R^9$; preferably, $R^4$ is selected from hydrogen, halogen; more preferably, $R^4$ is hydrogen or fluorine;

$R^5$ is selected from hydrogen, halogen, cyano, C1-C8 alkyl, C3-C8 cyclyl, 3-8 membered heterocyclyl, aryl, heteroaryl, formyl, —$C(O)R^{10}$, carboxyl, alkenyl, alkynyl, —$OR^{10}$, —$NR^8R^9$, —$OC(O)NR^8R^9$, —$C(O)OR^{10}$, —$C(O)NR^8R^9$, —$NR^8C(O)R^{10}$, —$NR^{10}C(O)NR^8R^9$, —$S(O)mR^{10}$, —$NR^8S(O)mR^{10}$, —$SR^{10}$, —$S(O)mNR^8R^9$ and —$NR^{10}S(O)mNR^8R^9$; preferably, $R^5$ is selected from hydrogen, halogen, C1-C6 alkyl and C3-C6 cyclyl; more preferably, $R^5$ is selected from hydrogen, halogen, C1-C4 alkyl and C3-C6 cyclyl; further preferably, $R^5$ is selected from hydrogen and halogen; most preferably, $R^5$ is fluorine;

$R^6$, $R^7$, $R^x$ are each independently selected from hydrogen, C1-C8 alkyl, C1-C8 haloalkyl, heteroalkyl, C3-C8 cyclyl, 3-8 membered monocyclic heterocyclyl, monocyclic aryl, monocyclic heteroaryl, alkenyl and alkynyl; preferably, $R^6$, $R^7$, $R^x$ are each independently selected from hydrogen, C1-C6 alkyl and C1-C6 haloalkyl; more preferably, $R^6$, $R^7$, $R^x$ are each independently selected from hydrogen, C1-C4 alkyl and C1-C4 haloalkyl; further preferably, $R^6$, $R^7$, $R^x$ are each independently selected from hydrogen and C1-C4 alkyl;

G1 is selected from halogen, cyano, C1-C8 alkyl, C3-C8 cyclyl, 3-8 membered heterocyclyl, aryl, heteroaryl, formyl, $-NR^8R^9$, $-C(O)R^{10}$, carboxyl, alkenyl, alkynyl, $-OR^{10}$, $-OC(O)NR^8R^9$, $-C(O)OR^{10}$, $-C(O)NR^8R^9$, $-NR^{11}C(O)R^{10}$, $-NR^{11}C(O)NR^8R^9$, $-S(O)mR^{10}$, $-NR^{11}S(O)mR^{10}$, $-SR^{10}$, $-S(O)mNR^8R^9$ and $-NR^{11}S(O)mNR^8R^9$; preferably, G1 is selected from halogen, C1-C6 alkyl, $-OR^{10}$, $-NR^8R^9$; more preferably, G1 is selected from halogen, C1-C4 alkyl, $-OR^{10}$, $-NR^8R^9$, wherein the alkyl is optionally substituted by one or more substituents selected from halogen, $-OR^{16}$, $-NR^{13}R^{14}$; when two G1s are connected to the same carbon atom or two adjacent carbon atoms, the two G1s can form a 3-8 membered cyclyl together with the carbon atom(s) connected with them, preferably form a 3-6 membered cycloalkyl, the cycloalkyl formed is optionally substituted by one or more substituents selected from halogen, $OR^{16}$ and $-NR^{13}R^{14}$;

$R^8$, $R^9$, $R^{10}$, $R^{11}$, $R^{12}$, $R^{13}$, $R^{14}$, $R^{15}$, $R^{16}$ are each independently selected from the group consisting of hydrogen, C1-C8 alkyl, C1-C8 haloalkyl, heteroalkyl, C3-C8 cyclyl, 3-8 membered monocyclic heterocyclyl, monocyclic heteroaryl, monocyclic aryl, alkenyl and alkynyl, wherein $R^8$ and $R^9$, $R^{13}$ and $R^{14}$ may form a 3-7 membered heterocyclyl;

and m is 1 or 2;

wherein the following compounds (1) to (7) are excluded:

(1)

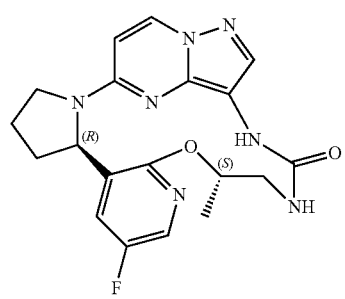

(2)

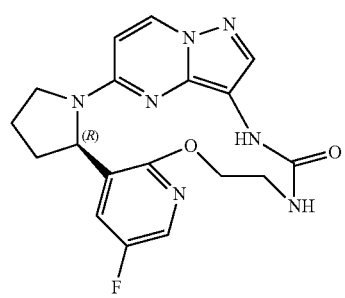

(3)

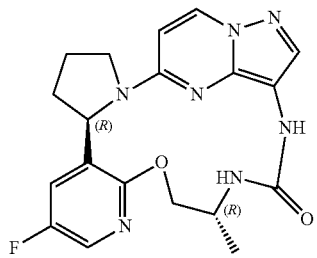

(4)

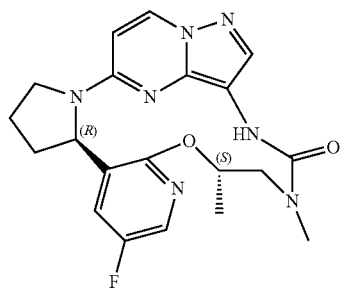

(5)

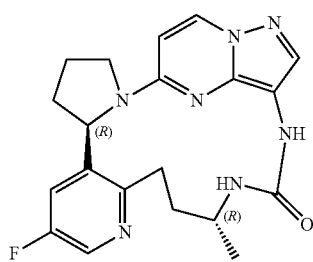

(6)

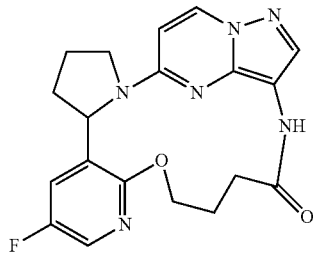

(7)

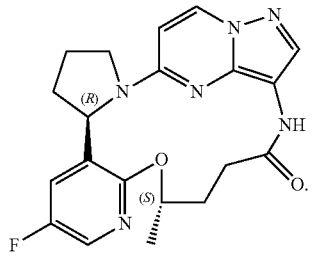

In a preferred embodiment of the present invention, a compound as shown in the above general formula I, and the isomers, prodrugs, solvates, stable isotopic derivatives or pharmaceutically acceptable salts thereof are provided, wherein:

$L_1$ is selected from $-NR^6C(O)-$, $-NR^6CON(R^7)-$, $-NR^6S(O)m-$ and $-NR^6S(O)mN(R^7)-$, of which $NR^6$ is connected with the nitrogen-containing heteroaryl substituted by $R^1$, $R^2$, $R^3$;

L₂ is selected from C1-C6 alkylene, C2-C6 alkenylene, C2-C6 alkynylene and C3-C6 cyclylene, wherein the alkylene, alkenylene, alkynylene and cyclylene can be optionally substituted by one or more G1;

L₃ is selected from a single bond and —O—;

$R^1$, $R^2$, $R^3$ are each independently selected from hydrogen, halogen, C1-C6 alkyl, C3-C6 cyclyl, 3-6 membered heterocyclyl, aryl and heteroaryl, wherein the alkyl, cyclyl, heterocyclyl, aryl or heteroaryl are optionally substituted by one or more substituents selected from halogen, cyano, C1-C6 alkyl, C3-C6 cyclyl and 3-6 membered heterocyclyl;

$R^4$ is selected from hydrogen, halogen, —$NR^8R^9$, —$OR^{10}$;

$R^5$ is selected from hydrogen, halogen, C1-C6 alkyl and C3-C6 cyclyl;

$R^6$, $R^7$ are each independently selected from hydrogen, C1-C6 alkyl, C1-C6 haloalkyl;

G1 is selected from halogen, C1-C6 alkyl, —$NR^8R^9$, —$OR^{10}$, wherein the alkyl is optionally substituted by one or more substituents selected from halogen, —$NR^{11}R^{12}$, —$OR^{16}$;

$R^8$, $R^9$, $R^{10}$, $R^{11}$, $R^{12}$ and $R^{16}$ are each independently selected from hydrogen, C1-C6 alkyl and C1-C6 haloalkyl;

and m is 1 or 2;

wherein the following compounds (1) to (7) are excluded:

(1)

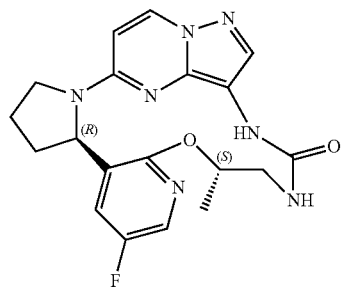

(2)

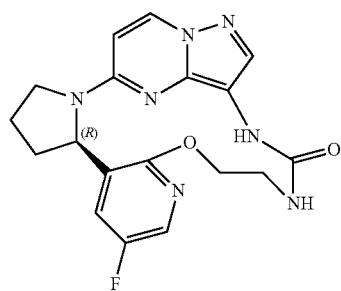

(3)

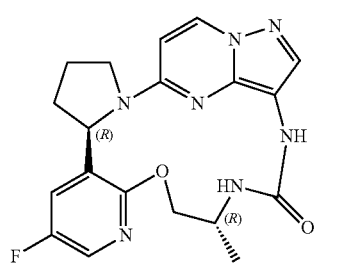

(4)

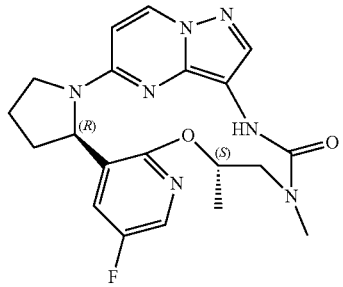

(5)

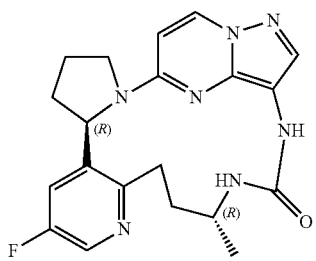

(6)

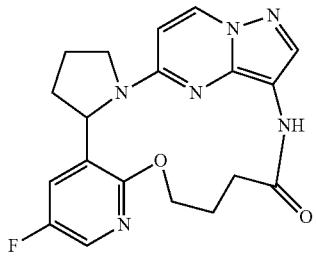

(7)

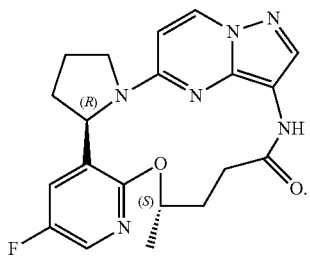

In another preferred embodiment of the present invention, a compound as shown in the above general formula I, and the isomers, prodrugs, solvates, stable isotopic derivatives or pharmaceutically acceptable salts thereof are provided, wherein:

L₁ is selected from —$NR^6C(O)$— and —$NR^6CON(R^7)$—, wherein $NR^6$ is connected with the nitrogen-containing heteroaryl substituted by $R^1$, $R^2$, $R^3$;

L₂ is selected from C1-C6 alkylene, C2-C6 alkenylene, C2-C6 alkynylene and C3-C6 cyclylene, wherein the alkylene, alkenylene, alkynylene and cyclylene can be optionally substituted by one or more G1;

L₃ is selected from a single bond and —O—;

$R^1$, $R^2$, $R^3$ are each independently selected from hydrogen, halogen, C1-C4 alkyl, C4-C6 cyclyl, 4-6 membered heterocyclyl, wherein the alkyl, cyclyl and heterocyclyl are optionally substituted by one or more substituents selected from halogen;

$R^4$ is selected from hydrogen, halogen, —$NR^8R^9$, —$OR^{10}$;

$R^5$ is selected from hydrogen, halogen, C1-C6 alkyl and C3-C6 cyclyl;

$R^6$, $R^7$ are each independently selected from hydrogen, C1-C6 alkyl, C1-C6 haloalkyl;
G1 is selected from halogen, C1-C6 alkyl, —$NR^8R^9$, —$OR^{10}$, wherein the alkyl is optionally substituted by one or more substituents selected from halogen, —$NR^{11}R^{12}$, —$OR^{16}$;
$R^8$, $R^9$, $R^{10}$, $R^{11}$, $R^{12}$ and $R^{16}$ are each independently selected from hydrogen, C1-C6 alkyl and C1-C6 haloalkyl;
wherein the following compounds (1) to (7) are excluded:

(1)
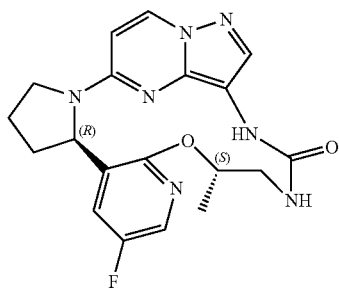

(2)
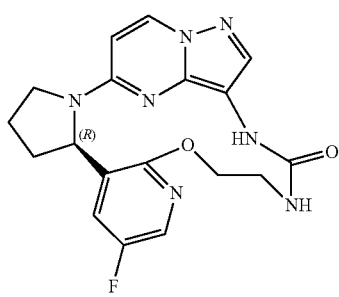

(3)
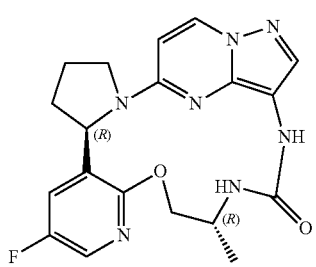

(4)
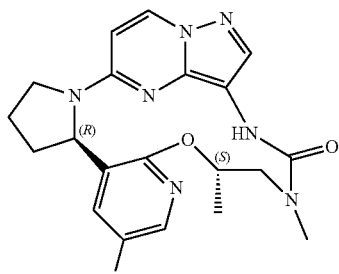

(5)
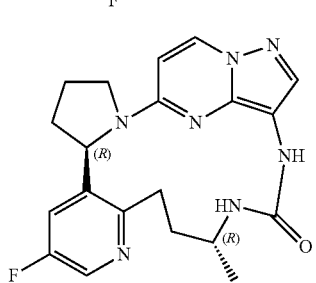

(6)
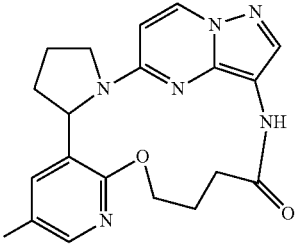

(7)
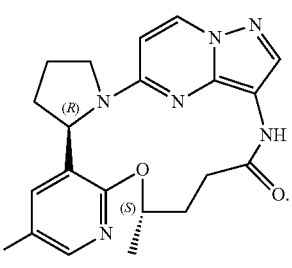

In another preferred embodiment of the present invention, a compound as shown in the above general formula I, and the isomers, prodrugs, solvates, stable isotopic derivatives or pharmaceutically acceptable salts thereof are provided, wherein:

$L_1$ is selected from —$NR^6CON(R^7)$—, of which $NR^6$ is connected with the nitrogen-containing heteroaryl substituted by $R^1$, $R^2$, $R^3$.
$L_2$ is selected from C1-C4 alkylene, C2-C4 alkenylene, C2-C4 alkynylene and C3-C4 cyclylene, wherein the alkylene, alkenylene, alkynylene and cyclylene can be optionally substituted by one or more G1;
$L_3$ is selected from a single bond and —O—;
$R^1$, $R^2$, $R^3$ are each independently selected from hydrogen, halogen and C1-C4 alkyl, wherein the alkyl is optionally substituted by one or more substituents selected from halogen;
$R^4$ is selected from hydrogen, halogen, —$NR^8R^9$, —$OR^{10}$;
$R^5$ is selected from hydrogen, halogen, C1-C6 alkyl and C3-C6 cyclyl;
$R^6$, $R^7$ are each independently selected from hydrogen, C1-C6 alkyl, C1-C6 haloalkyl;
G1 is selected from halogen, C1-C6 alkyl, —$NR^8R^9$, —$OR^{10}$, wherein the alkyl is optionally substituted by one or more substituents selected from halogen, —$NR^{11}R^{12}$, —$OR^{16}$;
$R^8$, $R^9$, $R^{10}$, $R^{11}$, $R^{12}$ and $R^{16}$ are each independently selected from the group consisting of hydrogen, C1-C6 alkyl and C1-C6 haloalkyl;
wherein the following compounds (1) to (5) are excluded:

(1)
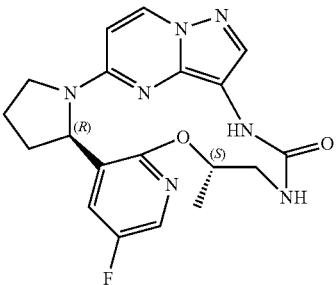

-continued (2)
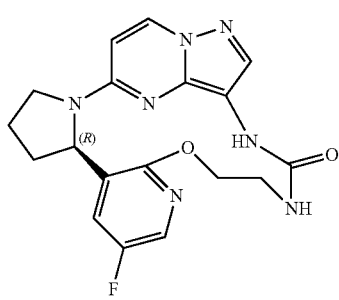

(3)
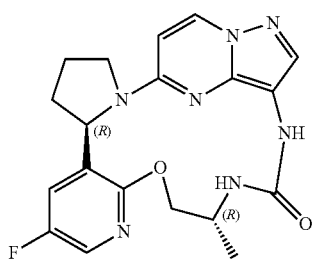

(4)
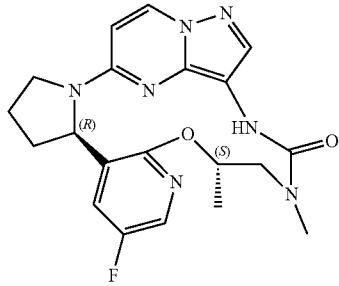

(5)
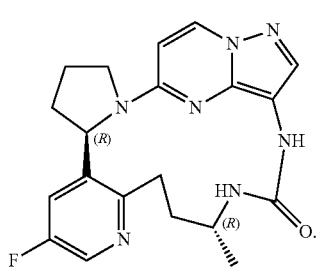

In another preferred embodiment of the present invention, a compound as shown in the above general formula I, and the isomers, prodrugs, solvates, stable isotopic derivatives or pharmaceutically acceptable salts thereof are provided, wherein:

$L_1$ is selected from —NR$^6$CON(R$^7$)—, of which NR$^6$ is connected with the nitrogen-containing heteroaryl substituted by R$^1$, R$^2$, R$^3$;

$L_2$ is selected from C1-C4 alkylene and C2-C4 alkenylene, wherein the alkylene and alkenylene can be optionally substituted by one or more G1;

$L_3$ is selected from a single bond and —O—;

R$^1$, R$^2$, R$^3$ are each independently selected from hydrogen, halogen and C1-C4 alkyl, wherein the alkyl is optionally substituted by one or more substituents selected from halogen;

R$^4$ is selected from hydrogen, halogen, —NR$^8$R$^9$, —OR$^{10}$;

R$^5$ is selected from halogen, C1-C4 alkyl and C3-C6 cyclyl;

R$^6$, R$^7$ are each independently selected from hydrogen, C1-C4 alkyl, C1-C4 haloalkyl;

G1 is selected from halogen, C1-C4 alkyl, —NR$^8$R$^9$, —OR$^{10}$, wherein the alkyl is optionally substituted by one or more substituents selected from halogen, —NR$^{11}$R$^{12}$, —OR$^{16}$;

R$^8$, R$^9$, R$^{10}$, R$^{11}$, R$^{12}$ and R$^{16}$ are each independently selected from hydrogen, C1-C4 alkyl, C1-C4 haloalkyl;

wherein the following compounds (1) to (5) are excluded:

(1)
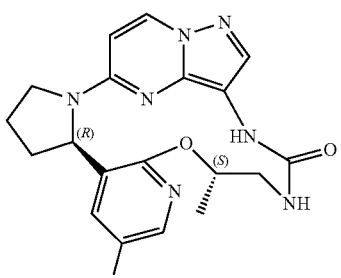

(2)
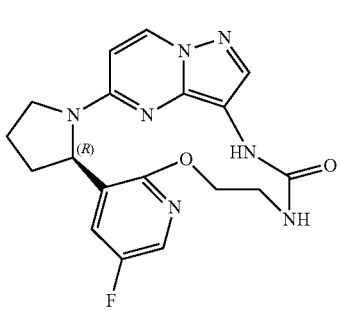

(3)
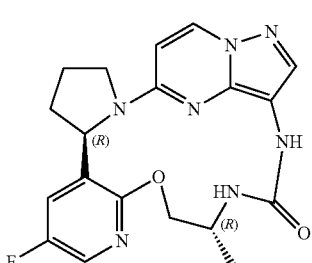

(4)
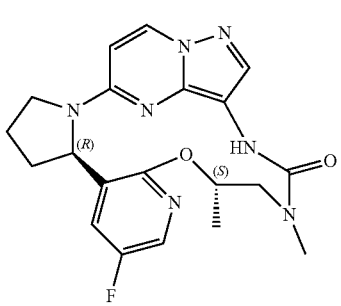

(5)
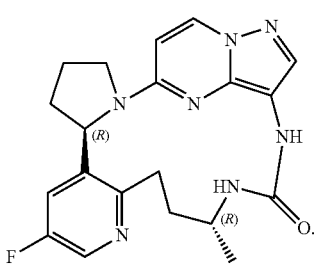

In another preferred embodiment of the present invention, a compound as shown in the above general formula I, and the isomers, prodrugs, solvates, stable isotopic derivatives or pharmaceutically acceptable salts thereof are provided, wherein:

$L_1$ is selected from —NR$^6$CON(R$^7$)—, of which NR$^6$ is connected with the nitrogen-containing heteroaryl substituted by R$^1$, R$^2$, R$^3$;

$L_2$ is selected from C1-C4 alkylene, wherein the alkylene can be optionally substituted by one or more G1;

$L_3$ is —O—;

R$^1$, R$^2$, R$^3$ are each independently selected from hydrogen, halogen and C1-C4 alkyl, wherein the alkyl is optionally substituted by one or more substituents selected from halogen;

R$^4$ is selected from hydrogen, halogen, —NR$^8$R$^9$, —OR$^{10}$;

R$^5$ is selected from hydrogen, halogen and C1-C4 alkyl;

R$^6$, R$^7$ are each independently selected from hydrogen, C1-C4 alkyl, C1-C4 haloalkyl;

G1 is selected from halogen, C1-C4 alkyl, —NR$^8$R$^9$, —OR$^{10}$, wherein the alkyl is optionally substituted by one or more substituents selected from halogen, —NR$^{11}$R$^{12}$, —OR$^{16}$;

R$^8$, R$^9$, R$^{10}$, R$^{11}$, R$^{12}$ and R$^{16}$ are each independently selected from hydrogen, C1-C4 alkyl and C1-C4 haloalkyl;

wherein the following compounds (1) to (4) are excluded:

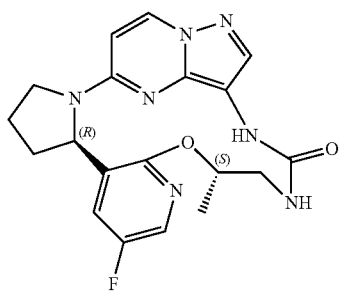
(1)

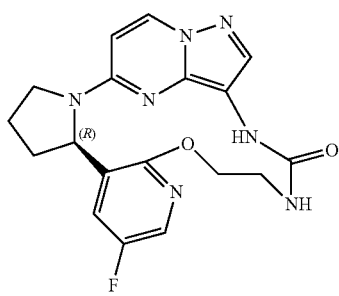
(2)

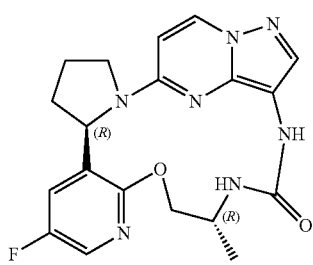
(3)

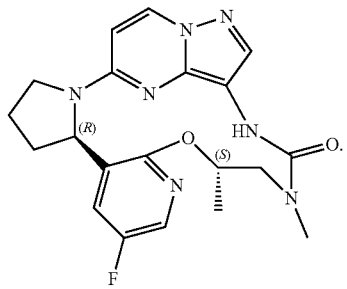
(4)

In another preferred embodiment of the present invention, a compound as shown in the above general formula I, and the isomers, prodrugs, solvates, stable isotopic derivatives or pharmaceutically acceptable salts thereof are provided, wherein:

$L_1$ is selected from —NR$^6$CON(R$^7$)—, of which NR$^6$ is connected with the nitrogen-containing heteroaryl substituted by R$^1$, R$^2$, R$^3$;

$L_2$ is selected from C1-C4 alkylene, wherein the alkylene can be optionally substituted by one or more G1;

$L_3$ is —O—;

R$^1$, R$^2$, R$^3$ are each independently selected from hydrogen and halogen;

R$^4$ is selected from hydrogen and halogen;

R$^5$ is selected from hydrogen, halogen and C1-C4 alkyl, and is located at the para position of $L_3$;

R$^6$, R$^7$ are each independently selected from hydrogen and C1-C4 alkyl;

G1 is selected from halogen, C1-C4 alkyl, wherein the alkyl is optionally substituted by one or more substituents selected from halogen, —NR$^{11}$R$^{12}$, —OR$^{16}$.

R$^{11}$, R$^{12}$ and R$^{16}$ are each independently selected from hydrogen, C1-C4 alkyl and C1-C4 haloalkyl; wherein the following compounds (1) to (4) are excluded:

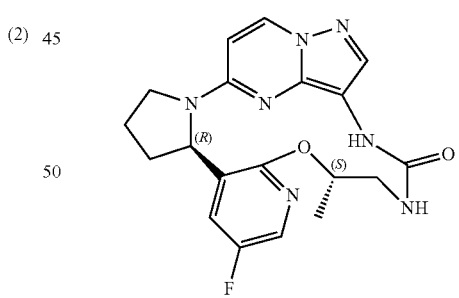
(1)

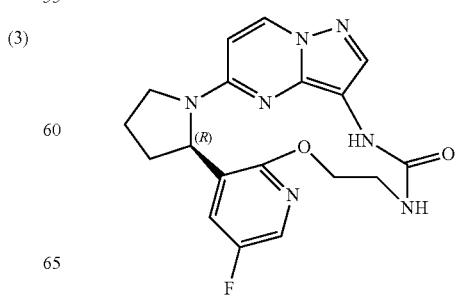
(2)

(3)

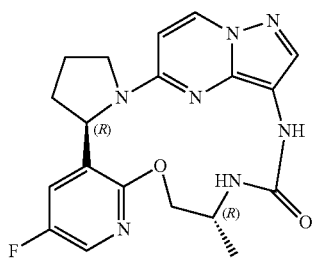

(4)

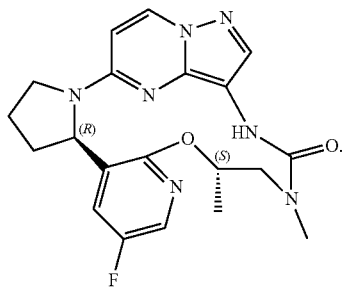

In another preferred embodiment of the present invention, a compound as shown in the above general formula I, and the isomers, prodrugs, solvates, stable isotopic derivatives or pharmaceutically acceptable salts thereof are provided, characterized in that the compounds are selected from:

1

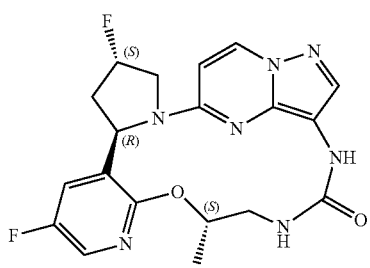

2

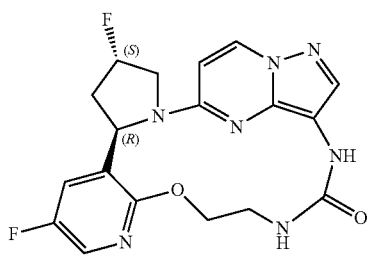

3

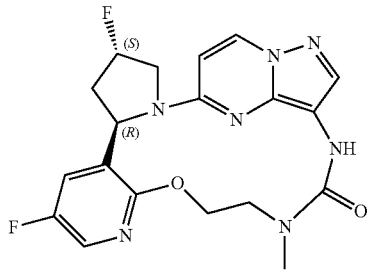

4

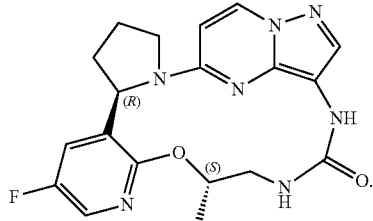

The invention further relates to a pharmaceutical composition comprising a compound according to any one of the embodiments mentioned above, or isomers, prodrugs, solvates, stable isotopic derivatives or pharmaceutically acceptable salts thereof, and a pharmaceutically acceptable carrier, diluent, excipient.

The present invention also relates to use of the compound according to any one of the embodiments mentioned above, and isomers, prodrugs, solvates, stable isotopic derivatives or pharmaceutically acceptable salts thereof, or use of the pharmaceutical composition according to the present invention, in the manufacture of a medicament for the treatment or prevention of TRK mediated diseases, such as cancer, especially hematological malignancies, lung cancer, breast cancer, ovarian cancer, prostate cancer, pancreatic cancer and glioma.

The present invention also relates to a method for treating or preventing TRK-mediated diseases (such as tumors, especially hematological malignancies, lung cancer, breast cancer, ovarian cancer, prostate cancer, pancreatic cancer, glioma), which comprises administering to the patient in need thereof therapeutically effective amount of the compound according to any one of the embodiments mentioned above, or isomers, prodrugs, solvates, stable isotopic derivatives or pharmaceutically acceptable salts thereof, or a pharmaceutical composition of the present invention.

Another aspect of the present invention relates to a compound represented by the general formula I as described in any one of the embodiments of the present invention, or isomers, prodrugs, solvates, stable isotopic derivatives thereof or pharmaceutically acceptable salts thereof, or a pharmaceutical composition comprising the same, for use in treating or preventing TRK-mediated diseases, such as tumors, especially hematological malignancies, lung cancer, breast cancer, ovarian cancer, prostate cancer, pancreatic cancer and glioma.

Another aspect of the present invention relates to a compound represented by the general formula I as described in any one of the embodiments of the present invention, or tautomers, mesomers, racemates, enantiomers, diastereomers thereof, or the mixture of the same, or pharmaceutically acceptable salts thereof, as a medicament for treatment and/or prevention of tumors and other diseases.

The preferred compounds according to the present invention include, but not limited to:

1. 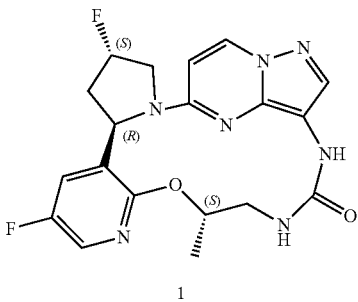

($2^2$R,$2^4$S,5S)-$2^4$,$3^5$-difluoro-5-methyl-4-oxa-7,9-diaza-1(5,3)-pyrazolo[1,5-a]pyrimidin-3(3,2)-pyridin-2(1,2)-pyrrolidincyclononan-8-one 2. 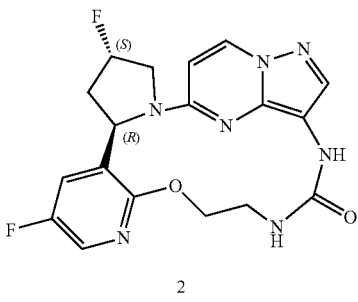

($2^2$R,$2^4$S)-$2^4$,$3^5$-difluoro-4-oxa-7,9-diaza-1(5,3)-pyrazolo[1,5-a]pyrimidin-3(3,2)-pyridin-2(1,2)-pyrrolidincyclononan-8-one 3. 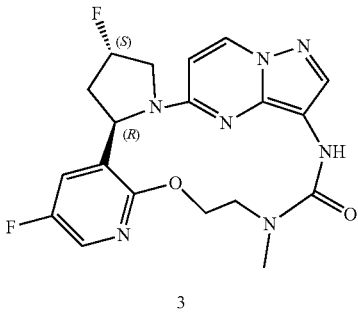

($2^2$R,$2^4$S)-$2^4$,$3^5$-difluoro-7-methyl-4-oxa-7,9-diaza-1(5,3)-pyrazolo[1,5-a]pyrimidin-3(3,2)-pyridin-2(1,2)-pyrrolidincyclononan-8-one 4. 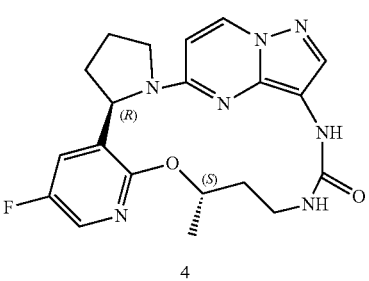

($2^2$R,5S)-$3^5$-fluoro-5-methyl-4-oxa-8,10-diaza-1(5,3)-pyrazolo[1,5-a]pyrimidin-3(3,2)-pyridin-2(1,2)-pyrrolidincyclodecan-9-one and isomers, prodrugs, solvates, stable isotopic derivatives or pharmaceutically acceptable salts thereof.

The compound represented by the general formula I of the present invention is a TRK inhibitor, so the compound represented by the general formula I of the present invention can be used to treat or prevent TRK-mediated diseases, such as tumors, especially hematological malignancies, lung cancer, breast cancer, ovarian cancer, prostate cancer, pancreatic cancer, brainglioma.

The present invention further relates to a pharmaceutical composition comprising a compound represented by the general formula I of the present invention or isomers, prodrugs, solvates, stable isotopic derivatives or pharmaceutically acceptable salts thereof and pharmaceutically acceptable carriers, diluents or excipients.

Another aspect of the present invention relates to use of the compound represented by the general formula I described in any one of the embodiments of the present invention, or isomers, prodrugs, solvates, stable isotopic derivatives or pharmaceutically acceptable salts thereof, or the pharmaceutical composition of the present invention in the manufacture of a medicament for treating or preventing TRK-mediated diseases, such as tumors, especially hematological malignancies, lung cancer, breast cancer, ovarian cancer, prostate cancer, pancreatic cancer and glioma.

Another aspect of the present invention relates to use of the compound represented by the general formula I or tautomers, mesomers, racemates, enantiomers, diastereomers thereof, or the mixture of the same, and pharmaceutically acceptable salts thereof, or the pharmaceutical composition comprising the same, in the manufacture of a medicament for treating and/or preventing tumors.

According to the present invention, the medicament can be in any dosage form, including but not limited to tablets, capsules, solutions, lyophilized preparations, injections.

The pharmaceutical preparation of the present invention can be administered in the form of a dosage unit containing a predetermined amount of active ingredient per dosage unit. Such a unit may contain, for example, 0.5 mg to 1 g, preferably 1 mg to 700 mg, particularly preferably 5 mg to 300 mg of the compound of the present invention according to the condition to be treated, the method of administration, and the age, weight and general conditions of the patient. The formulation can be administered in the form of a dosage unit containing a predetermined amount of active ingredient per dosage unit. Preferred dosage unit formulations are those containing the active ingredient in daily or divided doses or corresponding fractions thereof as indicated above. In addition, such pharmaceutical preparations can be prepared using methods known in the pharmaceutical field.

The pharmaceutical preparations of the present invention may be suitable for administration by any desired suitable method, such as oral (including oral or sublingual), rectal, nasal, topical (including oral, sublingual or transdermal), vaginal or parenteral (Including subcutaneous, intramuscular, intravenous or intradermal). All methods known in the pharmaceutical field can be used to prepare such formulations by, for example, combining the active ingredient with one or more excipients or one or more adjuvants.

The present invention also relates to a method for treating or preventing TRK-mediated diseases (such as tumors, especially hematological malignancies, lung cancer, breast cancer, ovarian cancer, prostate cancer, pancreatic cancer, glioma), which comprises administering to a patient in need therapeutically effective amount of a compound of the present invention or isomers, prodrugs, solvates, stable isotopic derivatives or pharmaceutically acceptable salts thereof, or a pharmaceutical composition of the present invention.

Another aspect of the present invention relates to a compound represented by general formula I, or isomers, prodrugs, solvates, stable isotopic derivatives or pharmaceutically acceptable salts thereof, or a pharmaceutical composition comprising the same, for use in the treatment or prevention of TRK-mediated diseases, such as tumors, especially hematological malignancies, lung cancer, breast cancer, ovarian cancer, prostate cancer, pancreatic cancer, and glioma.

Another aspect of the present invention relates to a compound represented by general formula I or tautomers, mesomers, racemates, enantiomers, diastereomers thereof, the mixture of the same, and pharmaceutically acceptable salts thereof for use in the treatment and/or prevention of tumors and other diseases.

Preparation Schemes

The present invention further provides methods for preparing the compounds.

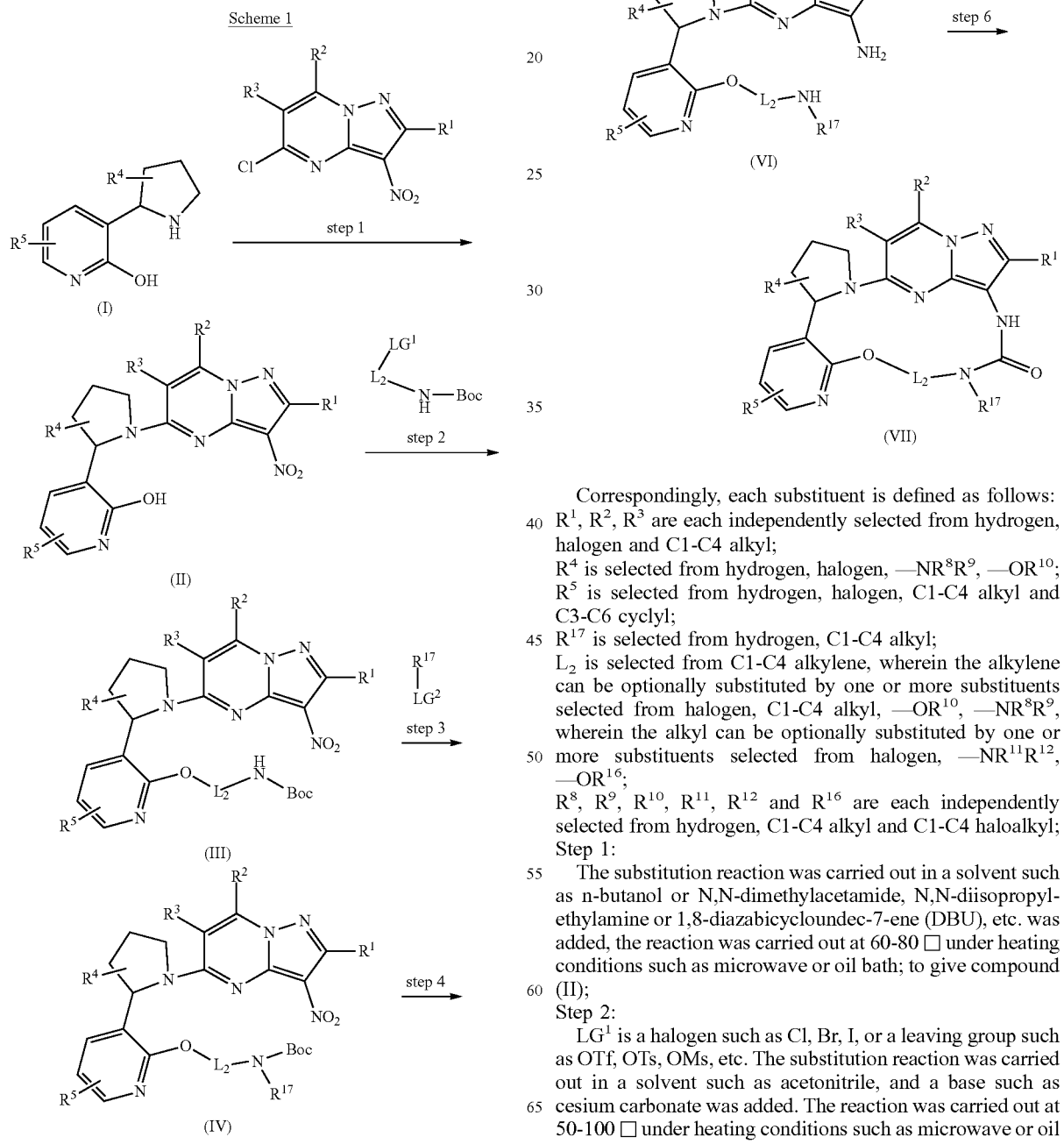

Correspondingly, each substituent is defined as follows:

$R^1$, $R^2$, $R^3$ are each independently selected from hydrogen, halogen and C1-C4 alkyl;

$R^4$ is selected from hydrogen, halogen, —$NR^8R^9$, —$OR^{10}$;

$R^5$ is selected from hydrogen, halogen, C1-C4 alkyl and C3-C6 cyclyl;

$R^{17}$ is selected from hydrogen, C1-C4 alkyl;

$L_2$ is selected from C1-C4 alkylene, wherein the alkylene can be optionally substituted by one or more substituents selected from halogen, C1-C4 alkyl, —$OR^{10}$, —$NR^8R^9$, wherein the alkyl can be optionally substituted by one or more substituents selected from halogen, —$NR^{11}R^{12}$, —$OR^{16}$;

$R^8$, $R^9$, $R^{10}$, $R^{11}$, $R^{12}$ and $R^{16}$ are each independently selected from hydrogen, C1-C4 alkyl and C1-C4 haloalkyl;

Step 1:

The substitution reaction was carried out in a solvent such as n-butanol or N,N-dimethylacetamide, N,N-diisopropylethylamine or 1,8-diazabicycloundec-7-ene (DBU), etc. was added, the reaction was carried out at 60-80 ☐ under heating conditions such as microwave or oil bath; to give compound (II);

Step 2:

$LG^1$ is a halogen such as Cl, Br, I, or a leaving group such as OTf, OTs, OMs, etc. The substitution reaction was carried out in a solvent such as acetonitrile, and a base such as cesium carbonate was added. The reaction was carried out at 50-100 ☐ under heating conditions such as microwave or oil bath; to give compound (III);

Step 3:

LG is a halogen such as Cl, Br, I, or a leaving group such as OTf, OTs, OMs, etc. The substitution reaction was carried out in a solvent such as N,N-dimethylacetamide, and a base such as sodium hydride was added at the same time, and the reaction was carried out at 0-25 ☐ to give compound (IV);

Step 4:

Zinc powder was used as the reducing agent in the reduction of the nitro group; a saturated ammonium chloride solution was added, and the reaction was carried out in a solvent such as dichloromethane at 0-25° C. to give compound (V);

Step 5:

Trifluoroacetic acid was used as the acid in the deprotection reaction of the tert-butoxycarbonyl group; the reaction was carried out in a solvent such as dichloromethane at 0-25 ☐ to give compound (VI).

Step 6:

N,N'-Carbonyldiimidazole or N,N'-carbonyldi(1,2,4-triazole) were used in the urea formation reaction of diamine (VI). Sometimes a base such as triethylamine was added, and the reaction was carried out in a solvent such as N,N-dimethylformamide, etc., at room temperature or 20-50 ☐ under heating conditions such as oil bath, to give compound (VII).

EMBODIMENTS

Definitions

Unless stated to the contrary, the following terms used in the description and the claims have the meanings as set forth below.

The expression "Cx-Cy" as used herein represents the range of the number of carbon atoms, wherein both x and y are integers. For example, C3-C8 cyclyl represents a cyclyl group having 3 to 8 carbon atoms, and C0-C2 alkyl represents an alkyl group having 0 to 2 carbon atoms, wherein C0 alkyl refers to a single bond.

The term "alkyl" as used herein refers to a saturated aliphatic hydrocarbon group, including linear and branched groups having 1 to 20 carbon atoms, for example, 1 to 18 carbon atoms, 1 to 12 carbon atoms, 1 to 8 carbon atoms, 1 to 6 carbon atoms or 1 to 4 carbon atoms. Non-limiting examples include methyl, ethyl, n-propyl, i-propyl, n-butyl, i-butyl, t-butyl, s-butyl, n-pentyl, 1,1-dimethyl propyl, 1,2-dimethyl propyl, 2,2-dimethyl propyl, 1-ethyl propyl, 2-methyl butyl, 3-methyl butyl, n-hexyl, 1-ethyl-2-methyl propyl, 1,1,2-trimethyl propyl, 1,1-dimethyl butyl, 1,2-dimethyl butyl, 2,2-dimethyl butyl, 1,3-dimethyl butyl, 2-ethyl butyl, and various branched isomers thereof, etc. Alkyl may be substituted or unsubstituted.

The term "alkenyl" as used herein refers to a linear, branched hydrocarbon group containing at least one carbon-carbon double bond, including linear and branched groups having 2 to 20 carbon atoms, for example, 2 to 18 carbon atoms, 2 to 12 carbon atoms, 2 to 8 carbon atoms, 2 to 6 carbon atoms or 2 to 4 carbon atoms. Wherein 1 to 3 carbon-carbon double bonds may be present and preferably 1 carbon-carbon double bond may be present. The term "C2-4 alkenyl" refers to alkenyl having 2 to 4 carbon atoms, including vinyl, propenyl, butenyl, buten-2-yl, 2-methylbutenyl. The alkenyl group may optionally be substituted.

The term "alkynyl" as used herein refers to a linear, or branched hydrocarbon group containing at least one carbon-carbon triple bond, including linear and branched groups having 2 to 20 carbon atoms, for example, linear and branched groups having 2 to 18 carbon atoms, 2 to 12 carbon atoms, 2 to 8 carbon atoms, 2 to 6 carbon atoms or 2 to 4 carbon atoms. Among them, 1 to 3 carbon-carbon triple bonds may be present and preferably 1 carbon-carbon triple bond may be present. The term "C2-4 alkynyl" refers to alkynyl having 2 to 4 carbon atoms, Non-limiting examples including acetenyl, propynyl, butynyl, butyn-2-yl and 3-methyl-1-butynyl.

The terms "alkylene", "alkenylene" and "alkynylene" as used herein respectively refer to substituted or unsubstituted alkyl, alkenyl and alkynyl groups having two terminal monovalent group cores, which are produced by removing one hydrogen atom from each of the two terminal carbon atoms; the "alkylene", "alkenylene", and "alkynylene" usually have 1-8 carbon atoms, preferably 1-6 carbon atoms, more preferably 1-4 carbon atoms. Non-limiting examples of "alkylene" include substituted or unsubstituted methylene, ethylene, propylene, butylene, etc.; non-limiting examples of "alkenylene" include substituted or unsubstituted vinylene, propenylene, butenylene etc. Non-limiting examples of "alkynylene" include substituted or unsubstituted ethynylene, propynylene, butynylene, etc.;

The term "cyclyl" used herein refers to all carbon saturated or partially unsaturated monocyclic or polycyclic hydrocarbyl groups, comprising 3 to 12 cyclic carbon atoms, such as 3 to 12, 3 to 10, 3 to 8 or 3 to 6 cyclic carbon atoms, or it can be 3, 4, 5, 6-membered rings. Non-limiting examples of monocyclic cyclyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, etc. Cyclyl may be substituted or unsubstituted.

The term "cyclylene" herein refers to a substituted or unsubstituted cyclic group having two terminal monovalent group cores, and the cyclic group has the definition mentioned above. Non-limiting examples of "cyclylene" include cyclopropylene, cyclobutylene, cyclopentylene, cyclopentenylene, cyclohexylene, cyclohexenylene, cyclohexadienylene, Cycloheptylene, cycloheptatrienylene, cyclooctylene, etc. The cyclylene group may be substituted or unsubstituted.

The term "heterocyclyl" used herein refers to a saturated or partially unsaturated monocyclic or polycyclic hydrocarbyl group, comprising 3 to 20 ring atoms, such as 3 to 16, 3 to 12, 3 to 10, 3 to 8 or 3 to 6 ring atoms, wherein one or more ring atoms are heteroatoms selected from nitrogen, oxygen or S(O)m (wherein m is an integer of 0 to 2), but excluding ring parts of —O—O—, —O—S— or —S—S—, and the remaining ring atoms are carbon. Preferably 3 to 12 ring atoms (of which 1 to 4 are heteroatoms) are comprised; more preferably, the heterocyclyl ring comprises 3 to 10 ring atoms, more preferably 3 to 8 ring atoms, further preferably 3 to 6 ring atoms; most preferred are 5-membered rings or 6-membered rings, wherein 1 to 4 members are heteroatoms, more preferably wherein 1 to 3 members are heteroatoms, and most preferably 1 to 2 members are heteroatoms. Non-limiting examples of monocyclic heterocyclyl include pyrrolidinyl, piperidyl, piperazinyl, morpholinyl, thiomorpholinyl, homopiperazinyl, etc. Bicyclic and polycyclic heterocyclic groups include spirocyclic, fused and bridged cyclic heterocyclic groups.

The term "spiroheterocyclyl" used herein refers to a 5 to 20 membered polycyclic heterocyclic group with one atom (referred to as a spiro atom) shared between monocyclic rings, wherein one or more of the ring atoms are heteroatoms selected from nitrogen, oxygen or $S(O)_m$ (wherein m is an integer of 0 to 2), and the rest of the ring atoms are carbon. They may contain one or more double bonds, but none of the rings has a completely conjugated π electron system. They are preferably 6 to 14 membered, and more preferably 7 to 10 membered. According to the number of spiro atoms shared between rings, spiroheterocyclic group are divided into mono-spiroheterocyclic group, bi-spiroheterocyclic group or poly-spiroheterocyclic group, preferably mono-spirocyclic group and bi-spirocyclic group, and more preferably 4 membered/4 membered, 4 membered/5 membered, 4 membered/6 membered, 5 membered/5 membered, or 5 membered/6 membered mono-spirocyclic group. Non-limiting examples of spiroheterocyclyl include

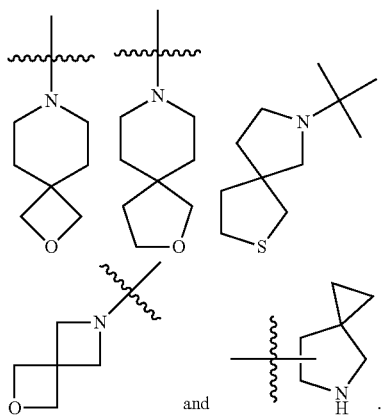

The term "fused heterocyclyl" used herein refers to a 5 to 20 membered polycyclic heterocyclic group wherein each ring in the system shares a pair of adjacent atoms with other rings in the system, one or more rings may contain one or more double bonds, but none of the rings has a completely conjugated π electron system, wherein one or more ring atoms are heteroatoms selected from nitrogen, oxygen or S(O)m (wherein m is an integer of 0 to 2), and the remaining ring atoms are carbon. They are preferably 6 to 14 membered, and more preferably 7 to 10 membered. According to the number of rings, they can be divided into bicyclic, tricyclic, tetracyclic or polycyclic fused heterocyclic group, and the fused heterocyclic groups are preferably bicyclic or tricyclic, more preferably 5 membered/5 membered, or 5 membered/6 membered bicyclic fused heterocyclic group. Non-limiting examples of fused heterocyclyl include:

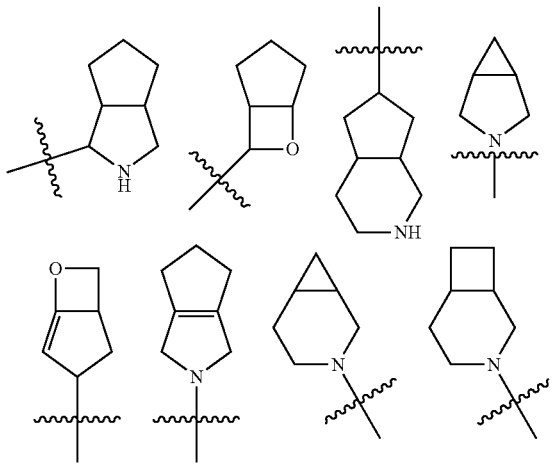

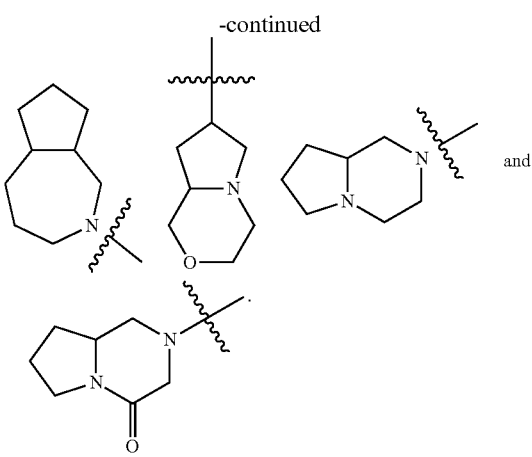

The heterocyclic ring may be fused to an aryl, a heteroaryl or a cyclic ring, in which the ring connected with the parent structure is a heterocyclic group, and the non-limiting examples include:

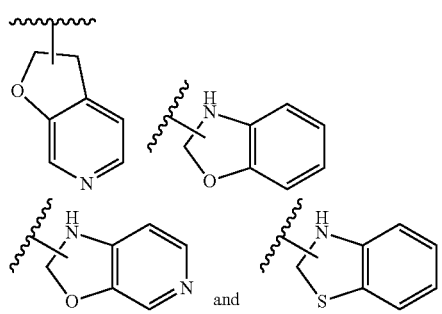

and the like.

The heterocyclyl may be substituted or unsubstituted.

The term "aryl" used herein refers to a 6 to 14 membered all-carbon monocyclic or condensed polycyclic (i.e., rings sharing adjacent pairs of carbon atoms) group, and a polycyclic (i.e., rings bearing adjacent pairs of carbon atoms) group having a conjugated π-electron system. Aryl groups can be monocyclic or polycyclic (i.e., can contain more than one ring). In the case of polycyclic aromatic rings, only one ring in the polycyclic system is required to be an aromatic ring, while the remaining rings may be saturated, partially saturated or unsaturated rings. The aryl group is preferably 6 to 10 membered, for example, phenyl and naphthyl, and most preferably phenyl. The aryl ring may be fused to a heteroaryl, a heterocyclyl or a cyclyl ring, in which the ring connected with the parent structure is an aryl ring, and the non-limiting examples include:

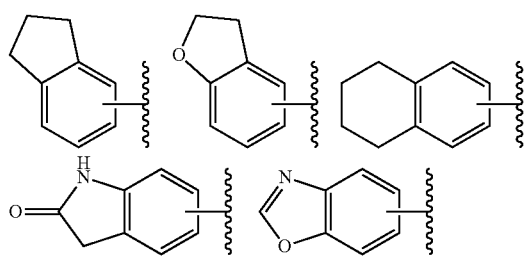

-continued

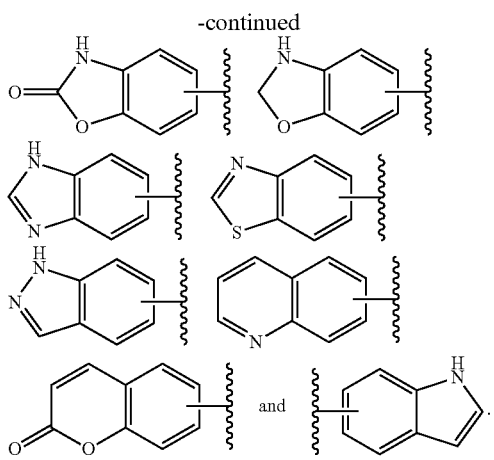

Aryl may be substituted or unsubstituted.

The term "arylene" refers to a substituted or unsubstituted aryl group having two monovalent group cores respectively, and the definition of the aryl group is the same as described above. Non-limiting examples of arylene groups are phenylene, naphthylene and the like. The arylene group may be optionally substituted or unsubstituted.

The term "heteroaryl" herein refers to a heteroaromatic system comprising 1 to 4 heteroatoms and 5 to 14 ring atoms, wherein the heteroatoms include oxygen, sulfur and nitrogen. Heteroaryl is preferably 5 to 10 membered, and more preferably 5 membered or 6 membered, for example: furyl, thienyl, pyridyl, pyrrolyl, N-alkylpyrrolyl, pyrimidinyl, pyrazinyl, imidazolyl, tetrazyl, oxazolyl, and isoxazolyl etc. The heteroaryl ring can be fused to an aryl, a heterocyclyl or a cyclyl ring, wherein the ring connected with the parent structure is a heteroaryl ring, and the non-limiting examples include:

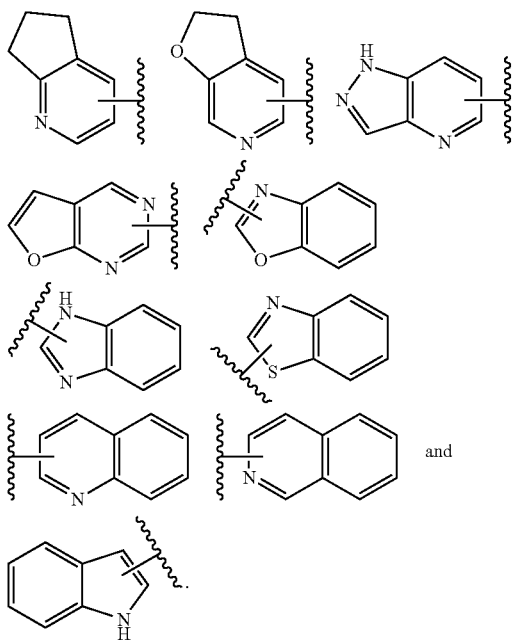

Heteroaryl may be substituted or unsubstituted.

The term "heteroarylene" used herein refers to a substituted or unsubstituted heteroaryl group having two monovalent group cores, respectively, and the definition of the heteroaryl group is the same as described above. Non-limiting examples of heteroarylene groups such as furanylene, thienylene, pyridylene, pyrrolylene, N-alkylpyrrolylene, pyrimidinylene, pyrazinylene, imidazolylidene, tetrazolylidene, oxazolylidene, isoxazolylidene, etc. The heteroarylene group may be optionally substituted or unsubstituted.

"halogen" used herein refers to fluorine, chlorine, bromine or iodine.

"Haloalkyl" refers to an alkyl substituent in which at least one hydrogen is replaced by a halogen group. Typical halogen groups include chlorine, fluorine, bromine and iodine. Examples of haloalkyl groups include fluoromethyl, fluoroethyl, chloromethyl, chloroethyl, 1-bromoethyl, difluoromethyl, trifluoromethyl, and 1,1,1-trifluoroethyl. It should be recognized that if a substituent is substituted with more than one halogen group, those halogen groups may be the same or different (unless otherwise stated).

"formyl" used herein refers to —CHO.

"carboxyl" used herein refers to —COOH.

"cyano" used herein refers to —CN.

The term "heteroalkyl" herein refers to a stable straight-chain or branched-chain hydrocarbon group consisting of a specified number of carbon atoms and at least one heteroatom selected from oxygen, nitrogen and sulfur. Among them, nitrogen and sulfur atoms may be oxidized optionally, nitrogen atoms may be quaternized optionally, and heteroatoms such as oxygen, nitrogen and sulfur may be located at any internal position of the heteroalkyl group, or at the position where the alkyl group is connected with the rest of the molecule. More than two heteroatoms may be independent or continuous.

The "optional" and "optionally" used herein means that an event or environment described subsequently may or may not necessarily occur, including cases where the event or environment occurs or does not occur. For example, "heterocyclyl optionally substituted by alkyl" means that alkyl may or may not necessarily exist, including cases where heterocyclyl is substituted by alkyl and is not substituted by alkyl.

The term "substituted" used herein refers that one or more hydrogen atoms, preferably at most 5 and more preferably 1 to 3 hydrogen atoms, in a group are replaced independently with a corresponding number of substituents. It goes without saying that, substituents are only located in their possible chemical positions, and a person skilled in the art can determine (experimentally or theoretically) possible or impossible substitutions without a lot of efforts. For example, amino or hydroxy groups having free hydrogen may be unstable when combined with carbon atoms having unsaturated (e.g. olefinic) bonds.

The substituent(s) include, but are not limited to the groups described above.

The term "pharmaceutical composition" used herein represents a mixture of one or more of the compounds described herein or physiologically/pharmaceutically acceptable salts or prodrugs thereof with other chemical components, as well as other components such as physiologically/pharmaceutically acceptable carriers and excipients. An object of the pharmaceutical compositions is to promote the administration of drugs to organisms, facilitate the absorption of active ingredients and thus exert biological activity.

The term "room temperature" in the present invention refers to 15-30° C.

The compounds of the invention can also exist as its isomer, prodrug, solvent complex or stable isotopic derivative. It will be understood by those skilled in the art that these isomers, prodrugs, solvent complexes or stable isotopic derivatives generally have activities similar to those of the compounds of the invention or pharmaceutically acceptable salts thereof, and are therefore covered by the protection scope of the present invention.

The term "a stable isotopic derivative" and "stable isotopic derivatives" used herein include: derivatives substituted with isotopes, such as derivatives obtained by substituting any hydrogen atom in Formula I with 1 to 5 deuterium atoms, derivatives substituted with isotopes obtained by substituting any carbon atom in Formula I with 1 to 3 carbon-14 atoms, or derivatives substituted with isotopes obtained by substituting any oxygen atom in Formula I with 1 to 3 oxygen-18 atoms.

The "pharmaceutically acceptable salts" as described in the present invention were discussed in Berge, et al., "Pharmaceutically acceptable salts," *J. Pharm. Sci.*, 66, 1-19 (1977), and it is obvious to pharmaceutical chemists that said salts are essentially non-toxic and can provide desired pharmacokinetic properties, palatability, absorption, distribution, metabolism or excretion, and the like.

The "pharmaceutically acceptable salts" according to the present invention can be synthesized through a common chemical method.

In general, the preparation of the salts can be achieved by reacting the compounds in the form of free base or acid with equivalent chemical equivalents or excess amounts of acids (inorganic or organic acids) or bases in suitable solvents or solvent compositions.

The "prodrug" as described in the present invention refers to a compound that can be converted into an original active compound after being metabolized in vivo. Representatively speaking, prodrugs are inactive substances, or have activity lower than the active parent compounds but can provide convenient operation, administration or improvement of metabolic properties.

The "isomer" of the present invention means that the compound of Formula I according to the present invention may have one or more asymmetric center and may be a racemate, a racemic mixture and a single diastereoisomer. The isomers such as stereoisomers and geometric isomers are all included in the present invention. The geometric isomers include cis- and trans-isomers.

The invention includes any polymorph of the compound or its salts, as well as any kind of hydrate or other solvate.

The term "tumor" used herein includes benign tumors and malignant tumors, such as cancer The term "cancer" used herein includes various tumors mediated by TRK, including but not limited to hematological malignancies, lung cancer, breast cancer, ovarian cancer, prostate cancer, pancreatic cancer, and glioma.

The term "therapeutically effective amount" refers to an amount including the compound of the present invention that can effectively treat or prevent related diseases mediated by TRK.

EXAMPLES

The present invention will be further illustrated by means of examples below, but is not therefore limited to the scope of the examples described. In the following examples, experimental methods without specific conditions noted are selected according to conventional methods and conditions or according to product instructions.

The structures of all the compounds according to the present invention can be identified by nuclear magnetic resonance ($^1$H NMR) and/or mass spectrometric detection (MS).

$^1$H NMR chemical shift (δ) is recorded as PPM (unit: 10-6 PPM). NMR is carried out by a Bruker AVANCE-400 spectrometer. Appropriate solvents include deuterated chloroform ($CDCl_3$), deuterated methanol ($CD_3OD$) and deuterated dimethylsulfoxide (DMSO-$d^6$), with tetramethylsilane as an internal standard (TMS).

The low resolution mass spectrogram (MS) is determined by an Agilent 1260HPLC/6120 mass spectrometer, using Agilent ZORBAX XDB-C18, 4.6×50 mm, 3.5 μm, at a gradient elution condition I: 0: 95% solvent A1 and 5% solvent B1, 1-2:5% solvent A1 and 95% solvent B1; 2.01-2.50: 95% solvent A1 and 5% solvent B1. The percentage is the volume percentage of a certain solvent based on the total solvent volume. Solvent A1: 0.01% formic acid aqueous solution; solvent B1: 0.01% formic acid solution in acetonitrile; and the percentage is the volume percentage of a solute based on the solution.

The thin-layer silica gel plate is a Yantai Yellow Sea HSGF254 or Qingdao Haiyang GF254 silica gel plates. The Yantai Yellow Sea 100-200 or 200-300 mesh silica gel is generally used as the support in the column chromatography.

The Preparative liquid chromatography (prep-HPLC) used is Waters SQD2 mass spectrometry guided high pressure liquid chromatography separator, XBridge-C18; 30×150 mm preparative column, 5 um; method 1: acetonitrile-water (0.2% formic acid), flow rate: 25 m/min; method 2: acetonitrile-water (0.8% ammonium bicarbonate), flow rate: 25 mL/min; The known starting raw materials of the present invention can be synthesized by or in accordance with methods known in the field, or can be purchased from companies such as Acros Organics, Aldrich Chemical Company, Accela ChemBio Inc., Shanghai Bide Pharmatech, Shanghai Aladdin Chemistry, Shanghai Meryer Chemistry, Accelerating Chemistry, Energy Chemistry, etc.

In the examples, unless stated otherwise, the solvents used in the reaction are all anhydrous solvents. Anhydrous tetrahydrofuran was obtained by the treatment of the commercially available tetrahydrofuran with metal sodium pieces as dehydrant, benzophenone as the indicator. The solution is refluxed under argon gas until it shows the color of bluish violet, then anhydrous tetrahydrofuran was distilled and collected, and stored at room temperature under the protection of nitrogen gas. The other anhydrous solvents are purchased from Energy Chemistry and Accelerating Chemistry. Transfer and use of all anhydrous solvents should be carried out under argon unless otherwise noted.

In the examples, the reactions are all carried out under an argon atmosphere or nitrogen atmosphere unless otherwise noted.

The argon atmosphere or nitrogen atmosphere means that the reaction flask is connected to an argon or nitrogen balloon with a volume of about 1 L.

The hydrogen atmosphere means that the reaction flask is connected to a hydrogen balloon with a volume of about 1 L.

The hydrogenation reaction generally requires that the container of the reaction be vacuumized and filled with hydrogen gas, and such operation should be repeated for 3 times.

The reaction was carried out at room temperature, and the temperature range is from 15° C. to 30° C., unless otherwise noted.

Thin-layer chromatography (TLC) is employed to monitor the reaction process in the examples. The developer system used for the reaction includes: A, dichloromethane and methanol system, and B: petroleum ether and ethyl acetate system, and the ratio by volume of the solvents is adjusted according to the polarity of the compound.

The eluent system for column chromatography and the developer system for thin-layer chromatography employed in the purification of compounds include: A, dichloromethane and methanol system, and B: petroleum ether and ethyl acetate system, the ratio by volume of the solvents is adjusted according to the polarity of the compound, and a small amount of triethyl amine and acidic or basic reagents and the like can also be added for adjustment.

Synthesis of Intermediate I (INT 1)

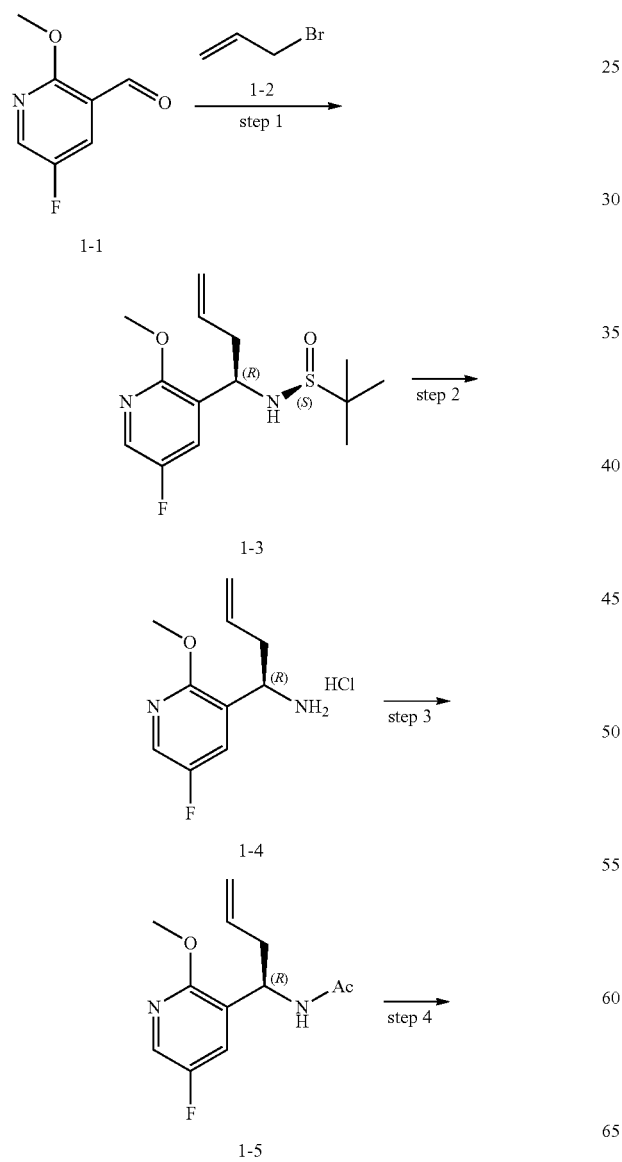

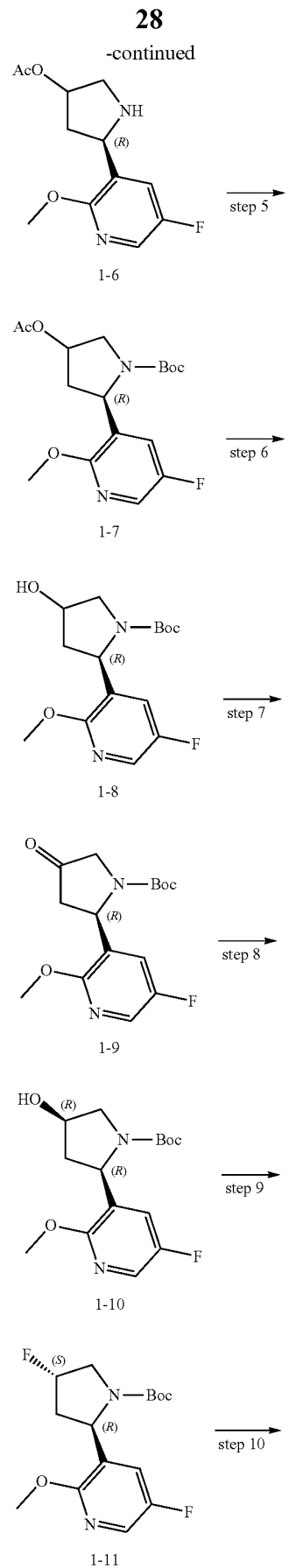

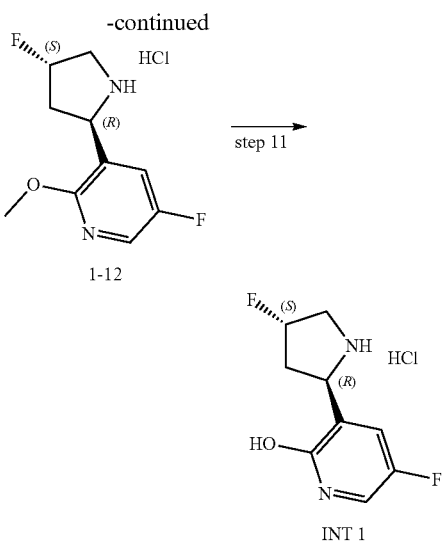

Step 1

(S)—N—((R)-1-(5-fluoro-2-methoxypyridin-3-yl) butan-3-en-1-yl)-2-methylpropan-2-sulfinamide 1-3

5-Fluoro-2-methoxynicotinaldehyde 1-1 (2.50 g, 16.10 mmol) was dissolved into tetrahydrofuran (35 mL). Indium powder (2.40 g, 20.90 mml), (S)-2-methylpropan-2-sulfinamide (2.33 g, 19.30 mmol) and tetraethoxytitanium (5.50 g, 24.20 mmol), were added sequentially under stirring. The reaction was stirred at 70 ☐ for 2 hours, cooled to 0 ☐, then 3-bromopropene 1-2 (3.10 g, 26.00 mmol) was added. The reaction was continued for 16 hours at 70☐. Then the reaction mixture was cooled in an ice bath and 150 mL of water was added to quench the reaction. The mixture was filtered and the filtrate as extracted with dichloromethane (200 ml×3). The organic phase as dried over anhydrous sodium sulfate, filtered, and purified by silica gel column (petroleum ether ethyl acetate=1:0~1:1) to give (S)—N—((R)-1-(5-fluoro-2-methoxypyridin-3-yl)butan-3-en-1-yl)-2-methylpropan-2-sulfinamide 1-3 (460 g, yellow oil). Yield: 95.2%

MS m/z (ESI): 301 [M+1];

$^1$H NMR (400 MHz, CDCl$_3$) δ 7.91 (d, J=3.2 Hz, 1H), 7.36-7.33 (m, 1H), 5.74-5.66 (m, 1H), 5.20-5.15 (m, 2H), 4.77-4.73 (m, 1H), 3.95 (s, 3H), 3.78-3.75 (m, 1H), 2.70-2.65 (m, 1H), 2.48-2.43 (m, 1H), 1.23 (s, 9H);

Step 2

(R)-1-(5-Fluoro-2-methoxyphenyl)but-3-en-1-amine hydrochloride 1-4

(S)—N—((R)-1-(5-Fluoro-2-methoxypyridin-3-yl)butan-3-en-1-yl)-2-methylpropan-2-sulfinamide 1-3 (4.60 g, 15.30 mmol) was dissolved into a solution of hydrogen chloride in dioxane (4 M, 25 mL) and methanol (25 mL). The reaction mixture was stirred at room temperature for 2 hours, until the reaction was finished. The solvent was removed under reduced pressure to give (R)-1-(5-fluoro-2-methoxyphenyl)but-3-en-1-amine hydrochloride 1-4 (5 g, white solid) as a crude product, theoretical yield: 3.56 g.

MS m/z (ESI): 197 [M+1];

Step 3

(R)—N-(1-(5-Fluoro-2-methoxypyridin-3-yl)but-3-en-1-yl)acetamide 1-5

(R)-1-(5-Fluoro-2-methoxyphenyl)but-3-en-1-aminehydrochloride 1-4 (3.56 g, 15.30 mmol) was dissolved into dichloromethane (50 mL) and triethylamine (3.86 g, 38.00 mmol) was added with stirring. The mixture was stirred at room temperature for 5 minutes, then acetic anhydride (2.34 g, 23.00 mmol) was added and stirring was continued at room temperature for 3 hours. Saturated aqueous sodium bicarbonate solution (30 mL) was added to quench the reaction and the mixture was extracted with dichloromethane (50 mL×3). The organic layer was washed with brine (50 mL), dried over anhydrous sodium sulfate, filtered and the filtrate was concentrated under reduced pressure to give (R)—N-(1-(5-fluoro-2-methoxypyridin-3-yl)but-3-en-1-yl)acetamide 1-5 (3.46 g, yellow solid), yield: 95.0%;

MS m/z (ESI): 239 [M+1];

$^1$H NMR (400 MHz, CDCl$_3$) δ 7.90 (d, J=2.8 Hz, 1H), 7.23-7.21 (m, 1H), 6.19 (d, J=7.6 Hz, 1H), 5.68-5.58 (m, 1H), 5.13-5.07 (m, 2H), 5.06-5.04 (m, 1H), 3.98 (s, 3H), 2.56-2.53 (m, 2H), 2.01 (s, 3H);

Step 4

(5R)-5-(5-fluoro-2-methoxypyridin-3-yl)pyrrolidin-3-yl acetate 1-6

(R)—N-(1-(5-Fluoro-2-methoxypyridin-3-yl)but-3-en-1-yl)acetamide 1-5 (3.46 g, 14.50 mmol) was dissolved into tetrahydrofuran (80 mL) and water (20 mL), iodine (11.08 g, 43.60 mmol) was added with stirring. The reaction was stirred at room temperature for 18 hours. Saturated aqueous sodium sulfite and sodium bicarbonate solution (100 mL) was added and stirred for 0.5 hour. The mixture was extracted with ethyl acetate (100 mL×3) and the combined organic layer was washed with brine (100 mL). The organic phase was dried over anhydrous sodium sulfate, filtered and the filtrate was concentrated to give (5R)-5-(5-fluoro-2-methoxypyridin-3-yl)pyrrolidin-3-yl acetate 1-6 (3.68 g, yellow solid) as a crude product;

MS m/z (ESI): 255 [M+1];

Step 5 tert-Butyl (2R)-4-acetoxy-2-(5-fluoro-2-methoxypyridin-3-yl)pyrrolidine-1-carboxylate 1-7

(5R)-5-(5-Fluoro-2-methoxypyridin-3-yl)pyrrolidin-3-yl acetate 1-6 (3.68 g, 14.50 mmol) was dissolved into tetrahydrofuran (15 mL) and water (15 mL). Aqueous sodium hydroxide solution (1 M, 10 mL) and di-tert-butyl dicarbonate (4.16 g, 18.90 mmol) were added with stirring. The reaction was stirred at room temperature for 18 hours and water (100 mL) was added to dilute the mixture. The reaction mixture was extracted with ethyl acetate (80 mL×3) and the combined organic layer was washed with water (100 mL×2) and brine (100 mL×2). The organic phase was dried over sodium sulfate, filtered, the filtrate was concentrated to give tert-butyl (2R)-4-acetoxy-2-(5-fluoro-2-methoxypyridin-3-yl)pyrrolidine-1-carboxylate 1-7 (6.0 g, yellow solid) as a crude product.

MS m/z (ESI): 377 [M+23];

Step 6 tert-Butyl (2R)-2-(5-fluoro-2-methoxypyridin-3-yl)-4-hydroxypyrrolidine-1-carboxylate 1-8 tert-Butyl (2R)-4-acetoxy-2-(5-fluoro-2-methoxypyridin-3-yl)pyrrolidine-1-carboxylate 1-7 (5.13 g, 14.50 mmol) was dissolved into methanol (40 mL) and aqueous sodium hydroxide solution (1 M, 20 mL) was added with stirring. The reaction mixture was stirred at room temperature for 2 hours. Water (100 mL) was added to dilute the reaction mixture, then it was extracted with ethyl acetate (100 mL×3). The combined organic phase was washed with water (100 mL×2) and brine (100 mL×2). The organic phase was dried over sodium sulfate and filtered. The filtrate was concentrated and purified by silica gel column (petroleum ether:ethyl acetate=1:0~1:1) to give tert-butyl (2R)-2-(5-fluoro-2-methoxypyridin-3-yl)-4-hydroxypyrrolidine-1-carboxylate 1-8 (2.45 g, yellow solid), the total yield over three steps is 54.1%;

MS m/z (ESI): 335 [M+23];

$^1$H NMR (400 MHz, CDCl$_3$) δ 7.87 (d, J=7.6 Hz, 1H), 7.38-7.14 (m, 1H), 5.12-4.93 (m, 1H), 4.49-4.41 (m, 1H), 3.93 (s, 3H), 3.75-3.52 (m, 2H), 2.53-2.41 (m, 1H), 1.98-1.91 (m, 1H), 1.46 (s, 4H), 1.18 (s, 5H);

Step 7 tert-Butyl (R)-2-(5-fluoro-2-methoxypyridin-3-yl)-4-oxopyrrolidine-1-carboxylate 1-9 tert-Butyl (2R)-2-(5-fluoro-2-methoxypyridin-3-yl)-4-hydroxypyrrolidine-1-carboxylate 1-8 (2.45 g, 7.85 mmol) was dissolved into dichloromethane (40 mL), Dess-Martin periodinane (4.16 g, 9.82 mmol) was added at room temperature. The reaction mixture was stirred at room temperature for 18 hours and dichloromethane (50 ml) was added to dilute it. The mixture was washed with saturated aqueous sodium sulfite solution (30 mL) and brine (50 mL) successively. The organic phase was dried over anhydrous sodium sulfate, filtered and the filtrate was concentrated to give tert-butyl (R)-2-(5-fluoro-2-methoxypyridin-3-yl)-4-oxopyrrolidine-1-carboxylate 1-9 (2.40 g, yellow oil), yield: 99.0%;

MS m/z (ESI): 333 [M+23];

$^1$H NMR (400 MHz, CDCl$_3$) δ 7.93 (s, 1H), 7.27-7.25 (m, 1H), 5.27-5.17 (m, 1H), 4.00-3.85 (m, 2H), 3.89 (s, 3H), 3.09-3.02 (m, 1H), 2.58-2.54 (m, 1H), 1.45 (s, 4H), 1.38 (s, 5H);

Step 8 tert-Butyl (2R,4R)-2-(5-fluoro-2-methoxypyridin-3-yl)-4-hydroxypyrrolidine-1-carboxylate 1-10 tert-Butyl (R)-2-(5-fluoro-2-methoxypyridin-3-yl)-4-oxopyrrolidine-1-carboxylate 1-9 (2.40 g, 7.70 mmol) was dissolved into methanol (15 mL) and sodium borohydride (0.29 g, 7.70 mmol) was added at −78 ☐. The reaction mixture was stirred at −78 ☐ for 1 hour. Saturated aqueous ammonium chloride solution (10 mL) was added to quench the reaction, and the mixture was extracted with ethyl acetate (50 mL×3). The combined organic phase was washed with water (100 mL×2) and brine (100 mL×2). The organic phase was dried over anhydrous sodium sulfate, filtered and the filtrate was concentrated to give tert-butyl (2R,4R)-2-(5-fluoro-2-methoxypyridin-3-yl)-4-hydroxypyrrolidine-1-carboxylate 1-10 (2.27 g, yellow oil), yield: 93.7%;

MS m/z (ESI): 335 [M+23];

$^1$H NMR (400 MHz, CDCl$_3$) δ 7.85 (s, 1H), 7.35-7.27 (m, 1H), 5.06-4.98 (m, 1H), 4.50-4.47 (m, 1H), 3.93 (s, 3H), 3.76-3.75 (m, 1H), 3.62-3.59 (m, 1H), 2.55-2.53 (m, 1H), 1.97-1.94 (m, 1H), 1.96-1.92 (m, 1H), 1.47 (s, 4H), 1.24 (s, 5H);

Step 9 tert-Butyl (2R,4S)-4-fluoro-2-(5-fluoro-2-methoxypyridin-3-yl)pyrrolidine-1-carboxylate 1-11 tert-Butyl (2R,4R)-2-(5-fluoro-2-methoxypyridin-3-yl)-4-hydroxypyrrolidine-1-carboxylate 1-10 (2.27 g, 7.30 mmol) was dissolved into dichloromethane (45 mL), diethylaminosulphur trifluoride (2.94, 18.25 mmol) was added at −78 ☐. The reaction mixture was warmed to room temperature slowly and then stirred for 16 hours. Saturated aqueous sodium bicarbonate solution (15 mL) was added to quench the reaction and the mixture was extracted with dichloromethane (50 mL×3). The combined organic phase was washed with water (100 mL×2) and brine (100 mL×2). The organic layer was dried over anhydrous sodium sulfate, filtered, the filtrate was concentrated. The residue was purified by silica gel column (petroleum ether:ethyl acetate=1:0~15:1) to give tert-butyl (2R,4S)-4-fluoro-2-(5-fluoro-2-methoxypyridin-3-yl)pyrrolidine-1-carboxylate 1-11 (1.40 g, colorless oil), yield: 51.8%;

MS m/z (ESI): 337 [M+23];

$^1$H NMR (400 MHz, CDCl$_3$) δ 7.89 (s, 0.6H), 7.87 (s, 0.4H), 7.26-7.21 (m, 1H), 5.28-5.03 (m, 2H), 4.13-4.08 (m, 1H), 3.95 (s, 3H), 3.71-3.59 (m, 1H), 2.78-2.73 (m, 1H), 1.98-1.81 (m, 1H), 1.46 (s, 3H), 1.21 (s, 6H);

Step 10

5-Fluoro-3-((2R,4S)-4-fluoropyrrolidin-2-yl)-2-methoxypyridine hydrochloride 1-12 tert-Butyl (2R,4S)-4-fluoro-2-(5-fluoro-2-methoxypyridin-3-yl)pyrrolidine-1-carboxylate 1-11 (1.40 g, 4.46 mmol) was dissolved into a solution of hydrogen chloride in methanol (4 M, 20 mL) and the reaction mixture was stirred at room temperature overnight. The solvent was removed under reduced pressure to give the target compound 5-fluoro-3-((2R,4S)-4-fluoropyrrolidin-2-yl)-2-methoxypyridine hydrochloride 1-12 (1.12 g, 4.46 mmol, yellow solid), yield: 100%;

MS m/z (ESI): 215 [M+1];

Step 11

5-Fluoro-3-((2R,4S)-4-fluoropyrrolidin-2-yl)pyridin-2-ol hydrochloride INT

5-Fluoro-3-((2R,4S)-4-fluoropyrrolidin-2-yl)-2-methoxypyridine hydrochloride 1-12 (1.12 g, 4.46 mmol) was dissolved into acetonitrile (40 mL), iodotrimethylsilane (1.8 g, 9.92 mmol) was added slowly. The reaction mixture was stirred at 50 ☐ for 1 hour. The solvent was removed under reduced pressure and water was added to quench the reaction. The aqueous phase was washed with ethyl acetate (30 mL×2) to remove the impurity and the resulting aqueous phase was concentrated to give 5-fluoro-3-((2R,4S)-4-fluoropyrrolidin-2-yl)pyridin-2-ol hydrochloride INT1 (0.95 g, 4.02 mmol, reddish brown oil), yield: 90.1%;

MS m/z (ESI): 201 [M+1];

¹H NMR (400 MHz, CD₃OD) δ 7.83 (s, 1H), 7.62 (s, 1H), 4.94-4.86 (m, 1H), 3.82-3.86 (m, z, 1H), 3.65-3.70 (m, 2H), 2.63-2.47 (m, 2H).

Example 1

(2²R,2⁴S,5S)-2⁴,3⁵-Difluoro-5-methyl-4-oxa-7,9-diaza-1(5,3)-pyrazolo[1,5-a]pyrimidin-3(3,2)-pyridin-2(1,2)-pyrrolidincyclononan-8-one

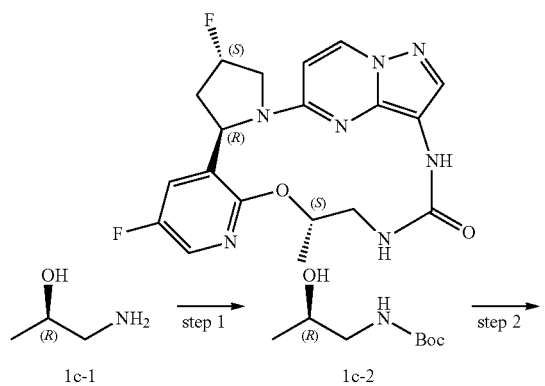

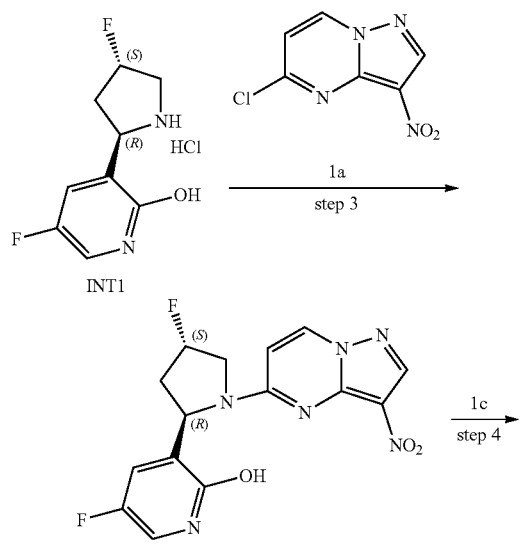

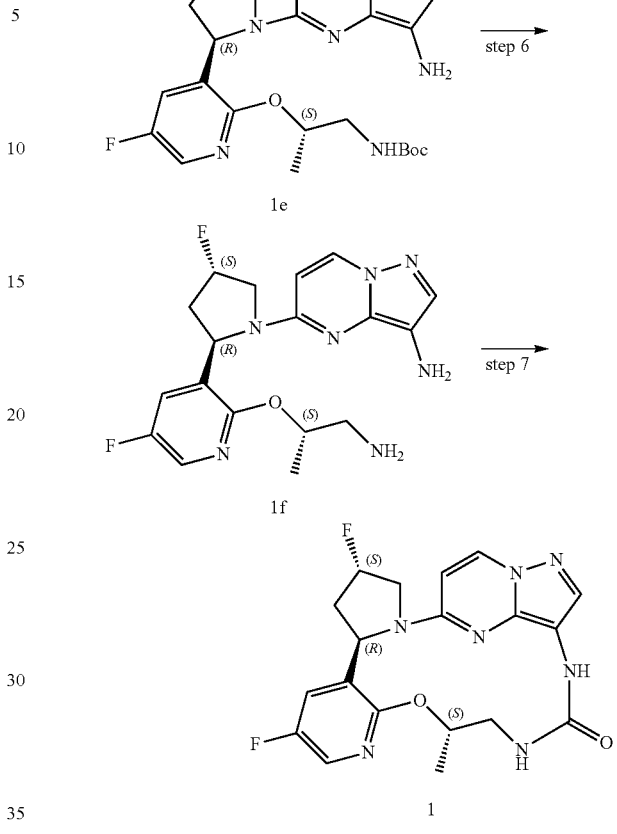

Step 1 tert-Butyl (R)-(2-hydroxypropyl)carbamate (R)-1-Aminopropan-2-ol 1c-1 (1.11 g, 14.80 mmol) was dissolved into tetrahydrofuran (80 mL), and di-tert-butyl dicarbonate (3.55 g, 16.30 mmol) was added to above solution slowly. The reaction mixture was stirred at room temperature for 30 minutes after the addition. When the reaction was finished, the mixture was concentrated directly to give tert-butyl (R)-(2-hydroxypropyl)carbamate 1c-2 (2.60 g, colorless liquid) as the crude product;

¹H NMR (400 MHz, CDCl₃) δ 3.28-3.25 (m, 1H), 3.04-2.97 (m, 1H), 2.29-2.27 (m, 1H), 1.45 (s, 9H), 1.18 (d, J=6.4 Hz, 3H);

Step 2

(R)-1-((tert-Butoxycarbonyl)amino)propan-2-yl 4-methylbenzenesulfonate tert-Butyl (R)-(2-hydroxypropyl)carbamate 1c-2 (3.90 g, 22.00 mmol) was dissolved into dichloromethane (40 mL), triethylamine (3.50 g, 34.50 mmol), 4-methylbenzenesulfonyl chloride (4.18 g, 22.00 mmol) and 4-(dimethylamino)pyridine (0.39 g, 3.20 mmol) were added to the reaction mixture, then the reaction mixture was stirred at 30° C. for 18 hours. The reaction mixture was washed with brine (30 mL×3), dried over anhydrous sodium sulfate and concentrated to give (R)-1-((tert-butoxycarbonyl)amino)propan-2-yl 4-methylbenzenesulfonate 1c (7.00 g, yellow oil, yellow solid after cooling) as the crude product;

MS m/z (ESI): 352 [M+23];

Step 3

5-Fluoro-3-((2R,4S)-4-fluoro-1-(3-nitropyrazolo[1,5-a]pyrimidin-5-yl)pyrrolidin-2-yl)pyridin-2-ol 1b 5-Fluoro-3-((2R,4S)-4-fluoropyrrolidin-2-yl)pyridin-2-ol hydrochloride INT1 (0.50 g, 2.00 mmol) and 5-chloro-3-nitropyrazolo[1,5-a]pyrimidine 1a (0.40 g, 2.00 mmol) were dissolved into butan-1-ol (25 mL), and N,N-diisopropyl-ethanamine (0.78 g, 6.00 mmol) was added. The reaction mixture was stirred at 40° C. for 3 hours, cooled to room temperature, filtered. The solid was dried to give 5-fluoro-3-((2R,4S)-4-fluoro-1-(3-nitropyrazolo[1,5-a]pyrimidin-5-yl)pyrrolidin-2-yl)pyridin-2-ol 1b (0.66 g, 1.82 mmol, yellow solid), yield: 91%;

MS m/z (ESI): 363 [M+1];

Step 4 tert-Butyl ((S)-2-((5-fluoro-3-((2R,4S)-4-fluoro-1-(3-nitropyrazolo[1,5-a]pyrimidin-5-yl)pyrrolidin-2-yl)pyridin-2-yl)oxy)isopropyl)carbamate 1d 5-Fluoro-3-((2R,4S)-4-fluoro-1-(3-nitropyrazolo[1,5-a]pyrimidin-5-yl)pyrrolidin-2-yl)pyridin-2-ol 1b (0.25 g, 0.69 mmol) and (R)-1-((tert-butoxycarbonyl)amino)propan-2-yl-4-methylbenzenesulfonate (0.68 g, 2.10 mmol) were dissolved into acetonitrile (15.0 mL), cesium carbonate (0.68 g, 2.10 mmol) was added. The reaction mixture was stirred at 80° C. for 3 hours and cooled to room temperature. The solvent was removed under reduced pressure and the residue was purified by Prep-TLC (ethyl acetate:petroleum ether=1:1) to give the target compound tert-butyl ((S)-2-((5-fluoro-3-((2R,4S)-4-fluoro-1-(3-nitropyrazolo[1,5-a]pyrimidin-5-yl)pyrrolidin-2-yl)pyridin-2-yl)oxy)propyl)carbamate d (0.10 g, 0.19 mmol, yellow solid), yield: 28%;

MS m/z (ESI): 542 [M+23];

$^1$H NMR (400 MHz, CDCl$_3$) δ 8.50 (s, 0.5H), 8.41 (s, 0.5H), 8.29 (d, J=8.0 Hz, 0.5H), 8.21 (d, J=8.0 Hz, 0.5H), 7.92 (s, 0.5H), 7.84 (s, 0.5H), 7.77-7.74 (m, 0.5H), 7.12-7.11 (m, 0.5H), 6.36 (d, J=8.0 Hz, 0.5H), 6.20 (d, J=8.0 Hz, 0.5H), 5.40-5.55 (m, 1H), 5.42-5.27 (m, 1H), 4.79-4.76 (m, 1H), 4.21-4.11 (m, 1H), 4.04-3.95 (m, 1H), 3.94-3.90 (m, 1H), 3.51-3.48 (m, 1H), 2.70-2.52 (m, 1H), 2.26-2.06 (m, 1H), 1.44 (d, J=6.0 Hz, 3H);

Step 5 tert-Butyl ((S)-2-((5-fluoro-3-((2R,4S)-4-fluoro-1-(3-aminopyrazolo[1,5-a]pyrimidin-5-yl)pyrrolidin-2-yl) pyridine-2-yl) oxy)isopropyl)carbamate 1e tert-Butyl ((S)-2-((5-fluoro-3-((2R,4S)-4-fluoro-1-(3-nitropyrazolo[1,5-a]pyrimidin-5-yl)pyrrolidin-2-yl)pyridin-2-yl)oxy)isopropyl)carbamate 1d (0.10 g, 0.19 mmol) was dissolved into methanol/dichloromethane (5.0 mL/5.0 mL), saturated ammonium chloride solution (5.0 mL) and zinc powder (0.18 g, 2.80 mmol) were added. The reaction mixture was stirred at room temperature for 1 hour, extracted with dichloromethane (10 mL×3) and the organic layer was dried over anhydrous sodium sulfate. The solvent was removed under reduced pressure to give tert-butyl ((S)-2-((5-fluoro-3-((2R,4S)-4-fluoro-1-(3-aminopyrazolo[1,5-a]pyrimidin-5-yl)pyrrolidin-2-yl) pyridine-2-yl) oxy)isopropyl) carbamate 1e (93 mg, 0.19 mmol, yellow oil), yield: 99%;

MS m/z (ESI): 490 [M+1];

Step 6

5-((2R,4S)-2-(2-(((S)-1-Aminopropan-2-yl)oxy)-5-fluoropyridin-3-yl)-4-fluoropyrrolidin-1-yl)pyrazolo[1,5-a]pyrimidin-3-amine 1f tert-Butyl ((S)-2-((5-fluoro-3-((2R,4S)-4-fluoro-1-(3-aminopyrazolo[1,5-a]pyrimidin-5-yl) pyrrolidin-2-yl) pyridine-2-yl) oxy)isopropyl)carbamatele (93 mg, 0.19 mmol) was dissolved into dichloromethane (5.0 mL), 2,2,2-trifluoroacetic acid (2.0 mL) was added at room temperature. The reaction mixture was stirred for 1 hour at room temperature. The solvent was removed under reduced pressure and the mixture was diluted with dichloromethane (5.0 mL). Triethylamine was added to neutralize the reaction system. The solvent was removed under reduced pressure to give the target compound 5-((2R,4S)-2-(2-(((S)-1-aminopropan-2-yl)oxy)-5-fluoropyridin-3-yl)-4-fluoropyrrolidin-1-yl)pyrazolo[1,5-a]pyrimidin-3-amine 1f (73 mg, 0.19 mmol, yellow oil) as a crude product;

MS m/z (ESI): 390 [M+1];

Step 7

($2^2$R,$2^4$S,5S)-$2^4$,$3^5$-Difluoro-5-methyl-4-oxa-7,9-diaza-1(5,3)-pyrazolo[1,5-a]pyrimidin-3(3,2)-pyridin-2(1,2)-pyrrolidincyclononan-8-one 5-((2R,4S)-2-(2-(((S)-1-Aminopropan-2-yl)oxy)-5-fluoropyridin-3-yl)-4-fluoropyrrolidin-1-yl)pyrazolo[1,5-a]pyrimidin-3-amine 1f (73 mg, 0.19 mmol) was dissolved into N,N-dimethylformamide (3.0 mL) and N,N-carbonyl diimidazole (62 mg, 0.38 mmol) was added. The reaction mixture was stirred at room temperature for 1 hour. The solvent was removed under reduced pressure and the residue was purified by Prep-TLC (dichloromethane:methanol=20:1) to give the target compound ($2^2$R,$2^4$S,5S)-$2^4$,$3^5$-difluoro-5-methyl-4-oxa-7,9-diaza-1(5,3)-pyrazolo[1,5-a]pyrimidin-3(3,2)-pyridin-2(1,2)-pyrrolidincyclononan-8-one 1 (11 mg, 0.03 mmol, yellow solid), yield: 14%;

MS m/z (ESI): 416 [M+1];

$^1$H NMR (400 MHz, CDCl$_3$) δ 8.25 (d, J=8.0 Hz, 1H), 7.88 (s, 1H), 7.64-7.62 (m, 1H), 7.59 (s, 1H), 7.14-7.11 (m, 1H), 6.35 (s, 1H), 6.20 (d, J=8.0 Hz, 1H), 5.68-5.61 (m, 1H), 5.60-5.52 (m, 1H), 4.23-4.14 (m, 1H), 4.04-3.98 (m, 1H), 3.88-3.83 (m, 1H), 3.03-2.84 (m, 2H), 2.26-2.06 (m, 2H), 1.44 (d, J=6.4 Hz, 3H).

Example 2

(2²R,2⁴S)-2⁴,35-difluoro-4-oxa-7,9-diaza-1(5,3)-pyrazolo[1,5-a]pyrimidin-3(3,2)-pyridin-2(1,2)-pyrrolidincyclononan-8-one

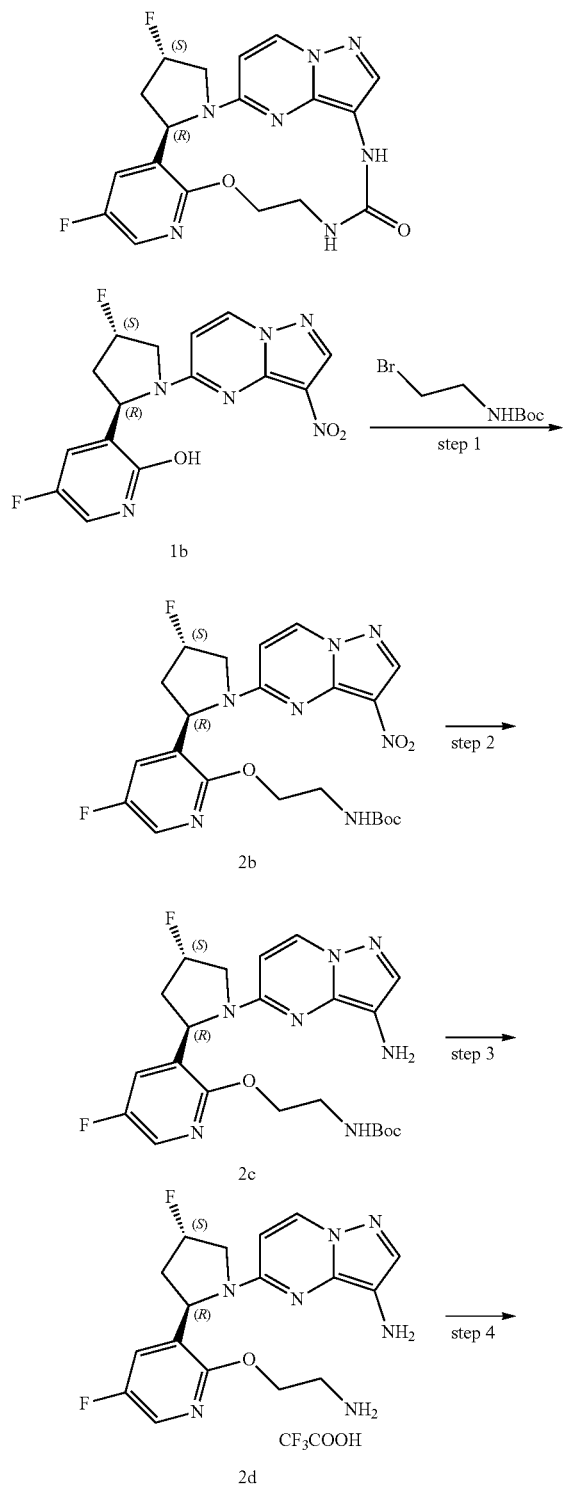

Step 1 tert-Butyl (2-((5-fluoro-3-((2R,4S)-4-fluoro-1-(3-nitropyrazolo[1,5-a]pyrimidin-5-yl)pyrrolidin-2-yl)pyridin-2-yl)oxy)ethyl)carbamate 2b 5-Fluoro-3-((2R,4S)-4-fluoro-1-(3-nitropyrazolo[1,5-a]pyrimidin-5-yl)pyrrolidin-2-yl)pyridin-2-ol 1b (0.25 g, 0.70 mmol) and cesium carbonate (0.65 g, 2.00 mmol) were added to acetonitrile (10 mL). The reaction mixture was stirred at 50 □ in an oil bath for 10 minutes, then tert-butyl (2-bromoethyl)carbamate 2a (0.22 g, 1.00 mmol) was added. The mixture was heated to 70 □ and stirred overnight. The reaction mixture was cooled, diluted with water (30 mL), and extracted with dichloromethane (50 mL×3). The combined organic phase was dried over anhydrous sodium sulfate, filtered to remove the drying agent and the filtrate was evaporated under reduced pressure. Purification of the residue by silica gel column (petroleum ether:ethyl acetate=19:1~3:2) gave the target compound tert-butyl (2-((5-fluoro-3-((2R,4S)-4-fluoro-1-(3-nitropyrazolo[1,5-a]pyrimidin-5-yl)pyrrolidin-2-yl)pyridin-2-yl)oxy)ethyl)carbamate 2b (0.11 g, 0.20 mmol, yellow solid), yield: 30%;

MS m/z (ESI): 506 [M+1];

¹H NMR (400 MHz, CDCl₃) δ 8.51 (s, 0.5H), 8.42 (s, 0.5H), 8.28-8.27 (m, 1H), 7.94 (s, 0.5H), 7.84 (s, 0.5H), 7.75-7.74 (m, 0.5H), 7.14-7.12 (m, 0.5H), 6.39-6.38 (m, 0.5H), 6.10-6.08 (m, 0.5H), 5.57 (s, 1H), 5.52-5.51 (m, 0.5H), 5.31-5.29 (m, 0.5H), 4.92-4.76 (m, 1.5H), 4.53-4.34 (m, 2.5H), 4.15-3.95 (m, 2H), 3.15-3.12 (m, 0.5H), 2.75-2.75 (m, 0.5H), 2.68-2.55 (m, 1H), 1.55 (s, 9H);

Step 2 tert-Butyl (2-((5-fluoro-3-((2R,4S)-4-fluoro-1-(3-aminopyrazolo[1,5-a]pyrimidin-5-yl)pyrrolidin-2-yl)pyridin-2-yl)oxy)ethyl)carbamate 2c tert-Butyl (2-((5-fluoro-3-((2R,4S)-4-fluoro-1-(3-nitropyrazolo[1,5-a]pyrimidin-5-yl)pyrrolidin-2-yl)pyridin-2-yl)oxy)ethyl)carbamate 2b (40 mg, 0.08 mmol), dichloromethane (2.0 mL), methanol (2.0 mL), saturated aqueous ammonium chloride (4.0 mL) and zinc powder (65 mg, 1.00 mmol) were mixed. The reaction mixture was stirred at room temperature for 30 minutes and extracted with dichloromethane (30 mL×2). The organic phase was washed with water (30 mL×3), dried over anhydrous sodium sulfate, and evaporated to give the target compound tert-butyl (2-((5-fluoro-3-((2R,4S)-4-fluoro-1-(3-aminopyrazolo[1,5-a]pyrimidin-5-yl)pyrrolidin-2-yl)pyridin-2-yl)oxy)ethyl)carbamate 2c (40 mg, 0.08 mmol, yellow solid) as a crude product;

MS m/z (ESI): 476 [M+1];

Step 3

5-((2R,4S)-2-(2-(2-Aminoethoxy)-5-fluoropyridin-3-yl)-4-fluoropyrrolidin-1-yl)pyrazolo[1,5-a]pyrimidin-3-amine 2,2,2-trifluoroacetate 2d tert-Butyl (2-((5-fluoro-3-((2R,4S)-4-fluoro-1-(3-aminopyrazolo[1,5-a]pyrimidin-5-yl)pyrrolidin-2-yl)pyridin-2-yl)oxy)ethyl)carbamate 2c (40 mg, 0.08 mmol) was dissolved into dichloromethane (1.0 mL), and trifluoroacetic acid (1.0 mL) was added. The reaction mixture was stirred at room temperature for 1 hour and evaporated under reduced pressure to give the target compound 5-((2R,4S)-2-(2-(2-aminoethoxy)-5-fluoropyridin-3-yl)-4-fluoropyrrolidin-1-yl)pyrazolo[1,5-a]pyrimidin-3-amine 2,2,2-trifluoroacetate 2d (30 mg, 0.08 mmol, yellow solid) as a crude product;

MS m/z (ESI): 376 [M+1];

Step 4

($2^2$R,$2^4$S)-$2^4$,$3^5$-Difluoro-4-oxa-7,9-diaza-1(5,3)-pyrazolo[1,5-a]pyrimidin-3(3,2)-pyridin-2(1,2)-pyrrolidincyclononan-8-one 5-((2R,4S)-2-(2-(2-Aminoethoxy)-5-fluoropyridin-3-yl)-4-fluoropyrrolidin-1-yl)pyrazolo[1,5-a]pyrimidin-3-amine 2,2,2-trifluoroacetate 2d (30 mg, 0.08 mmol) was dissolved into N,N-dimethylformamide (1 mL), triethylamine (0.2 mL) and N,N'-carbonyl diimidazole (10 mg, 0.06 mmol) were added. The reaction mixture was stirred at room temperature for 1 hour, extracted with ethyl acetate (50 mL×3) and washed with brine (5 mL×3). The organic phase was concentrated under reduced pressure, and purified by Prep-TLC (dichloromethane:methanol=10:1) to give the target compound ($2^2$R,$2^4$S)-$2^4$,$3^5$-difluoro-4-oxa-7,9-diaza-1(5,3)-pyrazolo[1,5-a]pyrimidin-3(3,2)-pyridin-2(1,2)-pyrrolidincyclononan-8-one 2 (8.0 mg, yellow solid), yield: 25%;

MS m/z (ESI): 402 [M+1];

$^1$H NMR (400 MHz, CDCl$_3$) δ 8.24 (d, J=7.6 Hz, 1H), 7.92-7.88 (m, 1H), 7.58 (s, 1H), 7.41-7.39 (m, 1H), 7.15-7.13 (m, 1H), 6.21 (d, J=7.6 Hz, 1H), 6.20-6.16 (m, 1H), 5.67-5.42 (m, 2H), 4.18-3.88 (m, 5H), 3.29-3.28 (m, 1H), 2.89-2.86 (m, 1H), 2.06-2.03 (m, 1H).

Example 3

($2^2$R,24S)-$2^4$,$3^5$-Difluoro-7-methyl-4-oxa-7,9-diaza-1(5,3)-pyrazolo[1,5-a]pyrimidin-3(3,2)-pyridin-2(1,2)-pyrrolidincyclononan-8-one

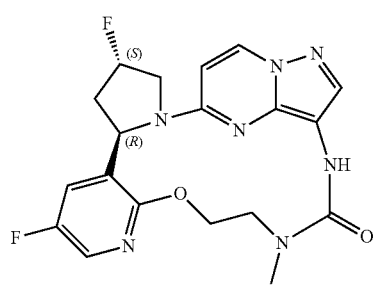

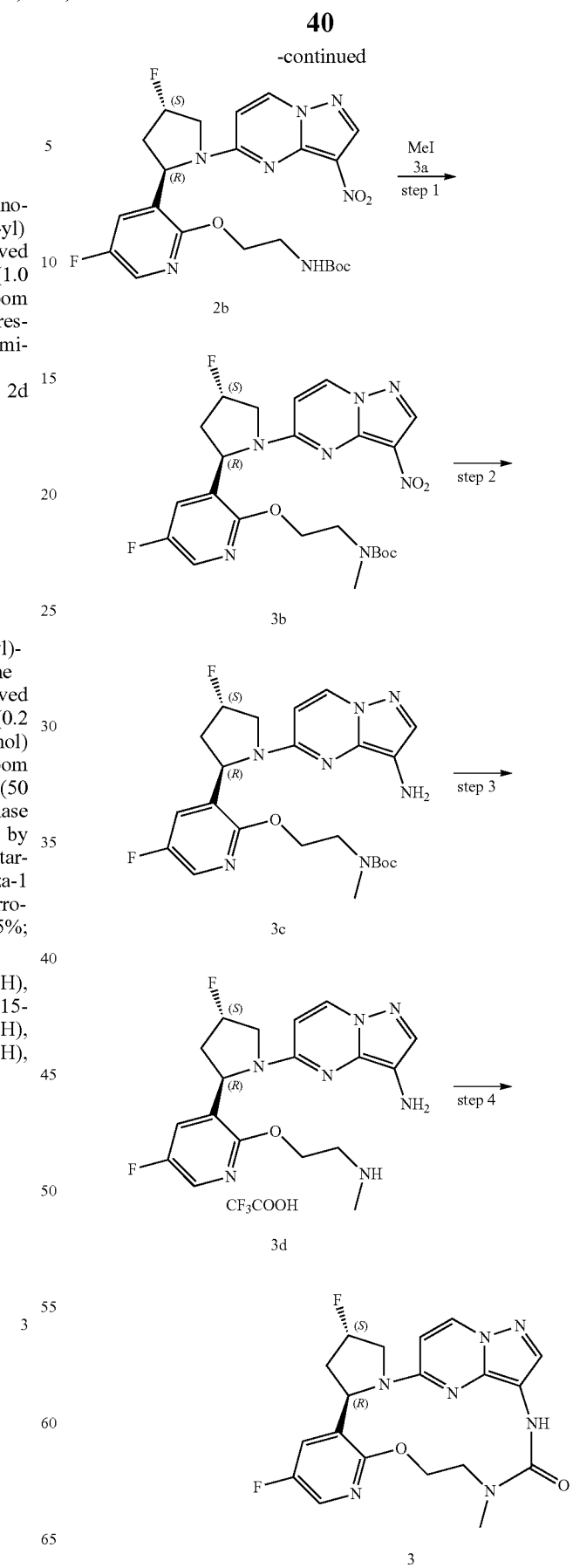

Step 1 tert-Butyl (2-((5-fluoro-3-((2R,4S)-4-fluoro-1-(3-nitropyrazolo[1,5-a]pyrimidin-5-yl)pyrrolidin-2-yl)pyridin-2-yl)oxy)ethyl)(methyl)carbamate 3b tert-Butyl (2-((5-fluoro-3-((2R,4S)-4-fluoro-1-(3-nitropyrazolo[1,5-a]pyrimidin-5-yl)pyrrolidin-2-yl)pyridin-2-yl)oxy)ethyl)carbamate 2b (20 mg, 0.14 mmol) was dissolved into N,N-dimethylformamide (2 mL) and sodium hydride (12 mg, 0.3 mmol, 60%, dispersed in mineral oil) was added. The reaction mixture was stirred at room temperature for 10 minutes. Methyl iodide 3a (42 mg, 0.3 mmol) was added and the mixture was stirred at room temperature for 30 minutes, extracted with ethyl acetate (10 mL×3), washed with water (10 mL×3) and the organic phase was dried over anhydrous sodium sulfate. The solvent was removed under reduced pressure to give tert-butyl (2-((5-fluoro-3-((2R,4S)-4-fluoro-1-(3-nitropyrazolo[1,5-a]pyrimidin-5-yl)pyrrolidin-2-yl)pyridin-2-yl)oxy)ethyl)(methyl)carbamate 3b (61 mg, 0.12 mmol, yellow solid). The product was used directly in the next step of the reaction without further purification.

MS m/z (ESI): 520 [M+1];

Step 2 tert-Butyl (2-((5-fluoro-3-((2R,4S)-4-fluoro-1-(3-aminopyrazolo[1,5-a]pyrimidin-5-yl)pyrrolidin-2-yl)pyridin-2-yl)oxy)ethyl)(methyl)carbamate 3c tert-Butyl (2-((5-fluoro-3-((2R,4S)-4-fluoro-1-(3-nitropyrazolo[1,5-a]pyrimidin-5-yl)pyrrolidin-2-yl)pyridin-2-yl)oxy)ethyl)(methyl)carbamate 3b (60 mg, 0.12 mmol), dichloromethane (2.0 mL), methanol (2.0 mL), saturated aqueous ammonium chloride solution (4.0 mL) and zinc powder (0.13 g, 2.00 mmol) were mixed and stirred at room temperature for 30 minutes. The reaction mixture was extracted with dichloromethane (30 mL×2), and the organic phase was washed with water (30 mL×3), dried over anhydrous sodium sulfate and concentrated under reduced pressure to give the target compound tert-butyl (2-((5-fluoro-3-((2R,4S)-4-fluoro-1-(3-aminopyrazolo[1,5-a]pyrimidin-5-yl)pyrrolidin-2-yl)pyridin-2-yl)oxy)ethyl)(methyl)carbamate 3c (60 mg, 0.12 mmol, yellow solid) as a crude product.

MS m/z (ESI): 490 [M+1];
$^1$H NMR (400 MHz, CDCl$_3$) δ 8.03-8.02 (m, 1H), 7.82-7.78 (m, 1H), 7.56 (s, 1H), 7.11-7.08 (m, 1H), 5.72-5.67 (m, 1H), 5.31-5.22 (m, 2H), 4.15-3.48 (m, 6H), 2.88 (s, 3H), 2.82-2.78 (m, 1H), 2.18-2.13 (m, 1H), 1.25 (s, 9H);

Step 3

5-((2R,4S)-4-Fluoro-2-(5-fluoro-2-(2-(methylamino)ethoxy)pyridin-3-yl)pyrrolidin-1-yl)pyrazolo[1,5-a]pyrimidin-3-amine 2,2,2-trifluoroacetate 3d tert-Butyl (2-((5-fluoro-3-((2R,4S)-4-fluoro-1-(3-aminopyrazolo[1,5-a]pyrimidin-5-yl)pyrrolidin-2-yl)pyridin-2-yl)oxy)ethyl)(methyl)carbamate 3c (60 mg, 0.12 mmol) was dissolved into dichloromethane (1.0 mL) and trifluoroacetic acid (1.0 mL) was added. The mixture was stirred at room temperature for 1 hour and concentrated under reduced pressure to give the target compound 5-((2R,4S)-4-fluoro-2-(5-fluoro-2-(2-(methylamino)ethoxy)pyridin-3-yl)pyrrolidin-1-yl)pyrazolo[1,5-a]pyrimidin-3-amine 2,2,2-trifluoroacetate 3d (40 mg, 0.10 mmol, yellow solid) as the crude product;

MS m/z (ESI): 390 [M+1];

Step 4

(2$^2$R,2$^4$S)-2$^4$,3$^5$-Difluoro-7-methyl-4-oxa-7,9-diaza-1(5,3)-pyrazolo[1,5-a]pyrimidin-3(3,2)-pyridin-2(1,2)-pyrrolidincyclononan-8-one 3

5-((2R,4S)-4-Fluoro-2-(5-fluoro-2-(2-(methylamino)ethoxy)pyridin-3-yl)pyrrolidin-1-yl)pyrazolo[1,5-a]pyrimidin-3-amine 2,2,2-trifluoroacetate 3d (40 mg, 0.10 mmol) was dissolved into N,N-dimethylformamide (1 mL), triethylamine (0.2 mL) and N,N-carbonyldiimidazole (16 mg, 0.10 mmol) were added. The reaction mixture was stirred at room temperature for 1 hour, extracted with ethyl acetate (50 mL×3) and washed with saturated solution of sodium chloride (50 mL×3). The organic phase was concentrated under reduced pressure. The residue was purified by Prep-TLC (dichloromethane:methanol=10:1) to give the target compound (2$^2$R,24S)-2$^4$,3$^5$-difluoro-7-methyl-4-oxa-7,9-diaza-1(5,3)-pyrazolo[1,5-a]pyrimidin-3(3,2)-pyridin-2(1,2)-pyrrolidincyclononan-8-one 3 (6.7 mg, white solid), yield: 21%;

MS m/z (ESI): 416 [M+1];
$^1$H NMR (400 MHz, CDCl$_3$) δ 8.22 (d, J=7.6 Hz, 1H), 7.82-7.80 (m, 2H), 7.16-7.14 (m, 1H), 6.14 (d, J=7.6 Hz, 1H), 5.74-5.52 (m, 3H), 4.15-3.48 (m, 6H), 3.08 (s, 3H), 2.82-2.78 (m, 1H), 2.27-2.23 (m, 1H).

Example 4

(2$^2$R,5S)-3$^5$-Fluoro-5-methyl-4-oxa-8,10-diaza-1(5,3)-pyrazolo[1,5-a]pyrimidin-3(3,2)-pyridin-2(1,2)-pyrrolidincyclodecan-9-one 4

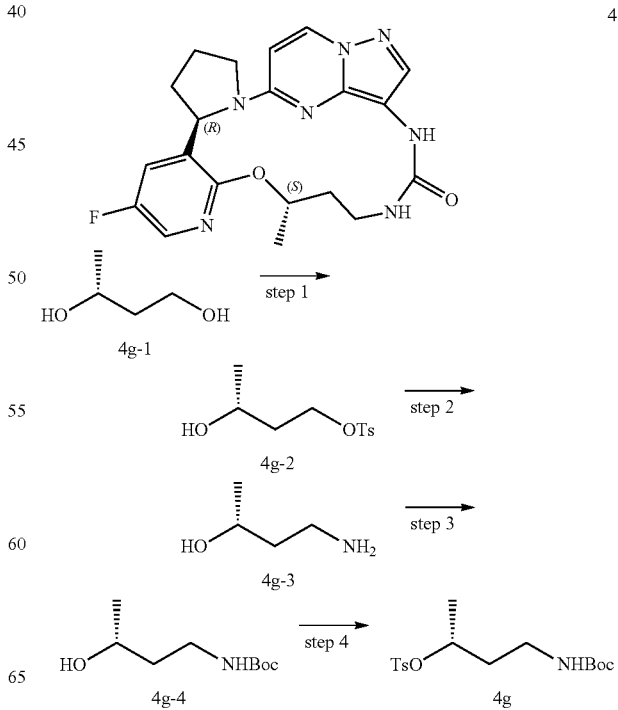

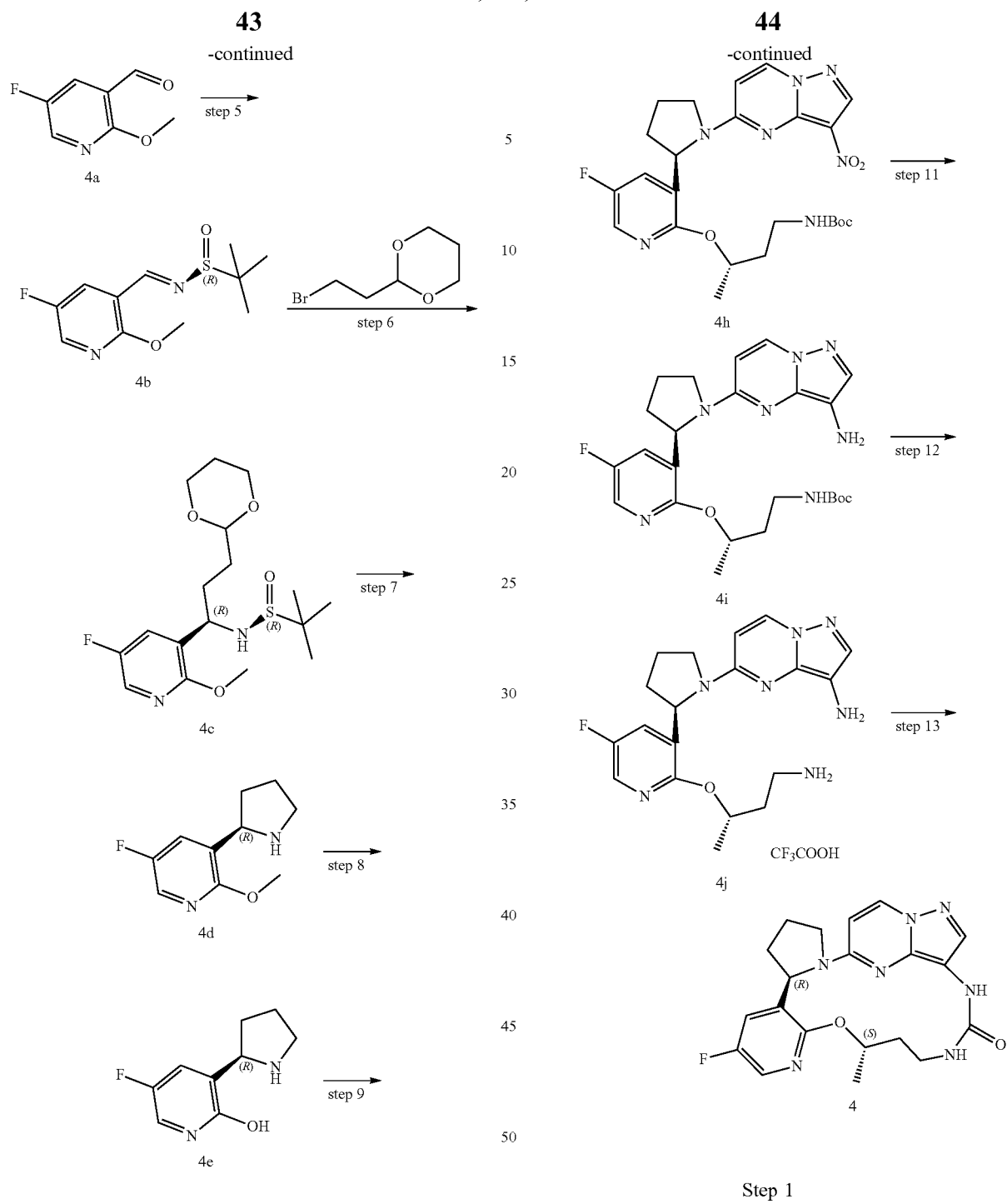

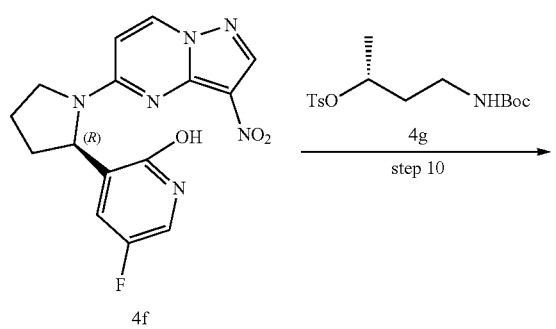

Step 1

(R)-3-Hydroxybutyl 4-methylbenzenesulfonate 4g-2

(3R)-Butan-1,3-diol 4g-1 (2.00 g, 22.22 mmol) was dissolved into dichloromethane (20 mL), and triethylamine (3.37 g, 33.33 mmol) was added. Then 4-methylbenzenesulfonyl chloride (4.46 g, 23.33 mmol) was added slowly at −20 □, and the reaction mixture was stirred at room temperature for 16 hours after the addition. The reaction mixture was diluted with water (50 mL) and extracted with dichloromethane (30 mL×3). The organic phase was washed with brine (30 mL×3), dried over anhydrous sodium sulfate, filtered and concentrated. The residue was purified by column chromatography (petroleum ether:ethyl acetate=100:

0~1:1) to give (R)-3-hydroxybutyl-4-methylbenzenesulfonate 4g-2 (3.80 g, yellow liquid), yield: 70%;

$^1$H NMR (400 MHz, CDCl$_3$) δ 7.87-7.76 (m, 2H), 7.44-7.30 (m, 2H), 4.33-4.16 (m, 1H), 4.15-4.07 (m, 1H), 4.03-3.88 (m, 1H), 2.45 (s, 3H), 1.90-1.78 (m, 1H), 1.76-1.63 (m, 1H), 1.22 (d, J=5.2 Hz, 3H);

Step 2

(R)-4-Aminobutan-2-ol 4g-3

(R)-3-Hydroxybutyl-4-methylbenzenesulfonate 4g-2 (3.50 g, 14.34 mmol) was dissolved into aqueous ammonia (25%, 50 mL) and the resulting mixture was stirred at 100 □ for 3 hours. The reaction mixture was cooled to room temperature and concentrated to give (R)-4-aminobutan-2-ol 4g-3 (1.28 g, 14.34 mmol) as a crude product;

MS m/z (ESI): 90 [M+1];

Step 3 tert-Butyl (R)-(3-hydroxybutyl)carbamate 4g-4

(R)-4-Aminobutan-2-ol 4g-3 (1.28 g, 14.34 mmol) was dissolved into 30 mL of tetrahydrofuran, triethylamine (2.20 g, 21.51 mmol) was added, then di-tert-butyl dicarbonate (3.30 g, 15.06 mmol) was added slowly. The reaction mixture was stirred for 1 hour at room temperature after the addition. After the reaction is finished, the reaction mixture was concentrated directly to give tert-butyl (R)-(3-hydroxybutyl)carbamate 4g-4 (2.71 g, colorless liquid) as a crude product;

$^1$H NMR (400 MHz, CDCl$_3$) δ 4.95-4.82 (m, 1H), 3.93-3.76 (m, 1H), 3.55-3.34 (m, 1H), 3.21-2.97 (m, 2H), 1.68-1.48 (m, 2H), 1.44 (s, 9H), 1.23 (d, J=5.2 Hz, 3H);

Step 4

(R)-4-((tert-Butoxycarbonyl)amino)butan-2-yl-4-methylbenzenesulfonate 4g tert-Butyl (R)-(3-hydroxybutyl)carbamate 4g-4 (0.38 g, 2.01 mmol) was dissolved into dichloromethane (5 mL), triethylamine (0.30 g, 3.01 mmol), 4-methylbenzenesulfonyl chloride (0.36 g, 1.91 mmol) and N,N-dimethyl-4-aminopyridine (25 mg, 0.20 mmol) were added. The reaction mixture was stirred at 30° C. for 18 hours after the addition, then diluted with dichloromethane (50 mL), washed with brine (30 mL×3) and dried over anhydrous sodium sulfate. The residue was purified by column chromatography (petroleum ether:ethyl acetate=100:0~65:35), to give (R)-4-((tert-butoxycarbonyl)amino)butan-2-yl-4-methylbenzenesulfonate 4g (0.10 g, yellow oil), yield: 15%;

MS m/z (ESI): 366 [M+Na];

Step 5

(R)—N-((5-Fluoro-2-methoxypyridin-3-yl)methylene)-2-methylpropan-2-sulfinamide 4b 5-Fluoro-2-methoxypyridine-3-carbaldehyde 4a (10.00 g, 64.5 mmol) was dissolved into dichloromethane (120 mL), cesium carbonate (42.00 g, 129.00 mmol) and (R)-2-methylpropan-2-sulfinamide (8.26 g, 67.70 mmol) were added. The reaction mixture was stirred at 30° C. for 4 hours after the addition, and filtered after the reaction is finished. The filtrate was concentrated directly to give (R)—N-((5-Fluoro-2-methoxypyridin-3-yl)methylene)-2-methylpropan-2-sulfinamide 4b (17.50 g, yellow oil), it was used directly to the next step without further purification;

MS m/z (ESI): 259 [M+1];

$^1$H NMR (400 MHz, CDCl$_3$) δ 8.88 (s, 1H), 8.16 (s, 1H), 7.98 (d, J=8.0 Hz, 1H), 4.01 (s, 3H), 1.27 (s, 9H);

Step 6

(R)—N—((R)-3-(1,3-Dioxan-2-yl)-1-(5-fluoro-2-methoxypyridin-3-yl)propyl)-2-methylpropane-2-sulfinamide 4c Magnesium chips (3.30 g, 136.00 mmol) was added into dry tetrahydrofuran (200 mL), and diisobutylaluminum hydride (0.3 mL, 1 M tetrahydrofuran solution) was added. The mixture was stirred at 50 □ for 15 minutes, then a solution of 2-(2-bromoethyl)-1,3-dioxane (26.50 g, 60 mmol) in tetrahydrofuran (50 mL) was added dropwise into the mixture, and the resulting mixture was stirred at 50° C. for 1 hour. The reaction mixture was further cooled slowly to −40 □, a solution of (R)—N-((5-Fluoro-2-methoxypyridin-3-yl)methylene)-2-methylpropan-2-sulfinamide 4b (17.50 g, 68.00 mmol) in tetrahydrofuran (50 mL) was added dropwise and stirred at −40° C. for 1 hour, warmed slowly to room temperature, stirred for another 1 hour, and quenched with citric acid aqueous solution (10%), then the mixture was extracted with methyl tert-butyl ether (400 mL). The organic phase was washed with saturated sodium bicarbonate aqueous solution and water, dried, filtered, and filtrate was concentrated to give (R)—N—((R)-3-(1,3-Dioxan-2-yl)-1-(5-fluoro-2-methoxypyridin-3-yl)propyl)-2-methylpropane-2-sulfinamide 4c (20.0 g, white solid), yield: 79%;

MS m/z (ESI): 375 [M+1];

$^1$H NMR (400 MHz, CDCl$_3$) δ 7.89 (s, 1H), 7.30 (d, J=8.0 Hz, 1H), 4.52-4.50 (m, 1H), 4.35-4.33 (m, 1H), 4.18-4.16 (m, 1H), 4.10-4.08 (m, 2H), 3.95 (s, 3H), 3.77-3.70 (m, 2H), 2.07-2.04 (m, 2H), 1.90-1.85 (m, 1H), 1.73-1.69 (m, 1H), 1.55-1.52 (m, 1H), 1.35-1.32 (m, 1H), 1.21 (s, 9H);

Step 7

(R)-5-fluoro-2-methoxy-3-(pyrrolidin-2-yl)pyridine 4d (R)—N—((R)-3-(1,3-Dioxan-2-yl)-1-(5-fluoro-2-methoxypyridin-3-yl)propyl)-2-methylpropan-2-sulfinamide 4c (20.00 g, 53.48 mmol) was dissolved into trifluoroacetic acid (100 mL) and water (10 mL). The reaction mixture was stirred at 20° C. for 1 hour. Then triethylsilane (80 mL) was added and stirring was continued at 20 □ for 16 hours. The solvent was evaporated and the residue was dissolved into water (300 mL), extracted with methyl tert-butyl ether (300 mL). The pH value of the aqueous phase was adjusted to approximately 13 with 40% aqueous sodium hydroxide solution and the mixture was extracted with dichloromethane (200 mL×3). The organic phase was washed with brine (100 mL), dried over anhydrous sodium sulfate, filtered and the filtrate was evaporated to give (R)-5-fluoro-2-methoxy-3-(pyrrolidin-2-yl)pyridine 4d (9.00 g, bright yellow oil), yield: 86%;

MS m/z (ESI): 197 [M+1];

$^1$H NMR (400 MHz, CDCl$_3$) δ 7.83 (s, 1H), 7.57 (d, J=8.8 Hz, 1H), 4.31-4.29 (m, 1H), 3.93 (s, 3H), 3.15-3.11 (m, 1H), 3.07-3.00 (m, 1H), 2.28-2.25 (m, 1H), 1.85-1.80 (m, 2H), 1.57-1.55 (m, 1H);

Step 8

(R)-5-Fluoro-3-(pyrrolidin-2-yl)pyridin-2-ol 4e (R)-5-fluoro-2-methoxy-3-(pyrrolidin-2-yl)pyridine 4d (1.20 g, 11.0 mmol) was dissolved into acetonitrile (20 mL), potassium iodide (3.70 g, 44.0 mmol) was added, then trimethylchlorosilane (2.30 g, 22.0 mmol) was added dropwise. The reaction mixture was stirred at 50° C. for 24 hours, then filtered and the filtrate was concentrated to give a solid, which was washed with dichloromethane:methanol=5:1, filtered and the filtrate was concentrated to give (R)-5-fluoro-3-(pyrrolidin-2-yl)pyridin-2-ol 4e (1.6 g, crude product, yellow solid);

MS m/z (ESI): 183 [M+1];

$^1$H NMR (400 MHz, DMSO-$d_6$) δ 9.23 (s, 1H), 8.61 (s, 1H), 7.83-7.81 (m, 1H), 7.76 (d, J=2.0 Hz, 1H), 4.48-4.44 (m, 1H), 3.25-3.17 (m, 2H), 2.22-2.18 (m, 1H), 2.09-2.07 (m, 2H), 1.93-1.91 (m, 1H);

Step 9

(R)-5-Fluoro-3-(1-(3-nitropyrazolo[1,5-a]pyrimidin-5-yl)pyrrolidin-2-yl)pyridin-2-ol 4f Using a similar procedure as described in the first step of Example 1, (R)-5-fluoro-3-(pyrrolidin-2-yl)pyridin-2-ol 4e was used instead of 5-fluoro-3-((2R,4S)-4-fluoropyrrolidin-2-yl)pyridin-2-ol hydrochloride INT1 to give the target product (R)-5-fluoro-3-(1-(3-nitropyrazolo[1,5-a]pyrimidin-5-yl)pyrrolidin-2-yl)pyridin-2-ol 4f;

MS m/z (ESI): 345 [M+1];

$^1$H NMR (400 MHz, DMSO-$d_6$) δ 8.82 (d, J=8.0 Hz, 0.44H), 8.64 (d, J=8.0 Hz, 0.56H), 8.63 (s, 0.56H), 8.56 (s, 0.44H), 7.56-7.55 (m, 0.56H), 7.45-7.44 (m, 0.44H), 7.29-7.27 (m, 1H), 6.75 (d, J=8.0 Hz, 0.44H), 6.14 (d, J=8.0 Hz, 0.56H), 5.40 (d, J=8.0 Hz, 0.44H), 5.07 (d, J=8.0 Hz, 0.56H), 4.05-3.95 (m, 2H), 3.81-3.75 (m, 1H), 3.62-3.55 (m, 1H), 2.41-2.35 (m, 1H), 2.26-2.15 (m, 1H), 1.95-1.90 (m, 1H);

Step 10 tert-Butyl ((S)-3-((5-fluoro-3-((R)-1-(3-nitro-6,7-dihydropyrazolo[1,5-a]pyrimidin-5-yl)pyrrolidin-2-yl)pyridin-2-yl)oxy)butyl)carbamate 4h Using a similar procedure as described in the second step of Example 1, (R)-5-fluoro-3-(1-(3-nitropyrazolo[1,5-a]pyrimidin-5-yl)pyrrolidin-2-yl)pyridin-2-ol 4f was used instead of 5-fluoro-3-((2R,4S)-4-fluoro-1-(3-nitropyrazolo[1,5-a]pyrimidin-5-yl)pyrrolidin-2-yl)pyridin-2-ol 1b to give the target product tert-butyl ((S)-3-((5-fluoro-3-((R)-1-(3-nitro-6,7-dihydropyrazolo[1,5-a]pyrimidin-5-yl)pyrrolidin-2-yl)pyridin-2-yl)oxy)butyl)carbamate 4h;

MS m/z (ESI): 516 [M+1];

Step 11 tert-Butyl ((S)-3-((5-fluoro-3-((R)-1-(3-amino-6,7-dihydropyrazolo[1,5-a]pyrimidin-5-yl)pyrrolidin-2-yl)pyridin-2-yl)oxy)butyl)carbamate Using a similar procedure as described in the third step of Example 1, tert-butyl ((S)-3-((5-fluoro-3-((R)-1-(3-nitro-6,7-dihydropyrazolo[1,5-a]pyrimidin-5-yl)pyrrolidin-2-yl)pyridin-2-yl)oxy)butyl)carbamate 4h was used instead of tert-butyl ((S)-2-((5-fluoro-3-((2R,4S)-4-fluoro-1-(3-nitropyrazolo[1,5-a]pyrimidin-5-yl)pyrrolidin-2-yl)pyridin-2-yl)oxy)propyl)carbamate 1c to give the target product tert-butyl ((S)-3-((5-fluoro-3-((R)-1-(3-amino-6,7-dihydropyrazolo[1,5-a]pyrimidin-5-yl)pyrrolidin-2-yl)pyridin-2-yl)oxy)butyl)carbamate 4i;

MS m/z (ESI): 488 [M+1];

Step 12

5-((R)-2-(2-(((S)-4-Aminobutan-2-yl)oxy)-5-fluoropyridin-3-yl)pyrrolidin-1-yl)-6,7-dihydropyrazolo[1,5-a]pyrimidin-3-amine trifluoroacetate 4j Using a similar procedure as described in the fourth step of Example 1, tert-butyl ((S)-3-((5-fluoro-3-((R)-1-(3-amino-6,7-dihydropyrazolo[1,5-a]pyrimidin-5-yl)pyrrolidin-2-yl)pyridin-2-yl)oxy)butyl)carbamate 4i was used instead of tert-butyl ((S)-2-((5-fluoro-3-((2R,4S)-4-fluoro-1-(3-aminopyrazolo[1,5-a]pyrimidin-5-yl)pyrrolidin-2-yl)pyridin-2-yl)oxy)isopropyl)carbamate 1d to give the target product 5-((R)-2-(2-(((S)-4-aminobutan-2-yl)oxy)-5-fluoropyridin-3-yl)pyrrolidin-1-yl)-6,7-dihydropyrazolo[1,5-a]pyrimidin-3-amine trifluoroacetate 4j;

MS m/z (ESI): 386 [M+1];

Step 13 ($2^2$R,5S)-$3^5$-Fluoro-5-methyl-4-oxa-8,10-diaza-1(5,3)-pyrazolo[1,5-a]pyrimidin-3(3,2)-pyridin-2(1,2)-pyrrolidincyclodecan-9-one 4

Using a similar procedure as described in the fifth step of Example 1, 5-((R)-2-(2-(((S)-4-aminobutan-2-yl)oxy)-5-fluoropyridin-3-yl)pyrrolidin-1-yl)-6,7-dihydropyrazolo[1,5-a]pyrimidin-3-amine trifluoroacetate 4j was used instead of 5-((2R,4S)-2-(2-(((S)-1-aminopropan-2-yl)oxy)-5-fluoropyridin-3-yl)-4-fluoropyrrolidin-1-yl)pyrazolo[1,5-a]pyrimidin-3-amine 1e to give the target product ($2^2$R,5S)-$3^5$-Fluoro-5-methyl-4-oxa-8,10-diaza-1(5,3)-pyrazolo[1,5-a]pyrimidin-3(3,2)-pyridin-2(1,2)-pyrrolidincyclodecan-9-one 4 (11.8 mg, 0.031 mmol, pale yellow solid); yield: 31%;

MS m/z (ESI): 412 [M+1];

$^1$H NMR (400 MHz, CDCl$_3$) δ 8.18 (d, J=7.8 Hz, 1H), 7.93-7.82 (m, 1H), 7.53 (s, 1H), 7.04-6.95 (m, 1H), 6.21 (d, J=7.8 Hz, 1H), 5.83 (s, 1H), 5.41-5.23 (m, 2H), 4.00-3.84 (m, 1H), 3.76-3.60 (m, 1H), 3.57-3.45 (m, 1H), 3.29-3.16 (m, 1H), 2.56-2.35 (m, 2H), 2.32-2.13 (m, 2H), 2.09-1.97 (m, 1H), 1.96-1.82 (m, 2H), 1.50 (d, J=5.2 Hz, 3H).

Biological Experiments

TRKA Activity Inhibition Test

The effect of the compounds of the invention on TRKA activity was evaluated by in vitro kinase assays The experimental methods were summarized as follows:

The in vitro activity of TRKA was measured by the use of a homogeneous time-resolved fluorescence (HTRF) kinase assay kit (Cisbio, NO. 62TKOPEC) through detecting the phosphorylation level of the substrate in the kinase reaction. The reaction buffer contained the following components: reaction buffer of the enzyme in the kit (1×), 5 mM MgCl$_2$, 1 mM DTT; The humanized recombined TRKA protein was expressed and purified by the purification and identification platform of Tsinghua university, and was diluted into kinase solution (3 ng/μl) with the reaction buffer. The substrate reaction solution comprised 0.23 μM biotin-labeled tyrosine kinase substrate and 8.4 μM ATP, which was diluted with reaction buffer. The detection buffer comprised 0.1 ng/μL cage antibody labelled with Eu3+ and 14.375 nM XL665 labeled with streptavidin, which was diluted with reaction buffer.

The compound was dissolved into 100% DMSO and diluted to 100 or 10 µM, then diluted with DMSO in 4 times serial dilution to a minimum concentration of 6.1 or 0.61 nM, and each concentration point was further diluted 40 times with the reaction buffer.

To the 384 well plate (Corning No. 4512), 4 µl of the solution of the test compound and 2 µl of the solution of TRKA kinase were added respectively, then mixed well and incubated at room temperature for 15 minutes. 4 µl of the solution of substrate was then added and the reaction mixture was incubated at room temperature for 60 minutes. A 10 µl detection buffer of the same volume as the reaction mixture was then added, the mixture was mixed well and allowed to stand for 30 minutes at room temperature. The reaction process was monitored at the wavelengths of 620 nm and 665 nm by Envision board reader (Perkin Elmer). The ratio of 665/620 was positively correlated with the phosphorylation level of the substrate, then TRKA kinase activity was determined. In this experiment, the group without TRKA kinase was used as the negative control, the group with TRKA kinase but without the test compound was used as the positive control (0% inhibition). The inhibition percentage of the test compound on the TRKA activity can be calculated by the following formula: The $IC_{50}$ value of the compound was calculated at 8 concentration points by use of XLfit software (ID Business Solutions Ltd. UK) through the following formula:

$$Y=\text{Bottom}+(\text{Top}-\text{Bottom})/(1+10^{((\log IC_{50}-X)*\text{slope factor})})$$

Of which Y is the inhibition percentage; X is the logarithm of the concentration of the compound to be tested; Bottom is the maximum inhibition percentage; Top is the minimum inhibition percentage; slope factor is the slope coefficient of the curve.

TRKA G595R Activity Inhibition Test:

The effect of the compounds of the invention on the activity of TRKA G595R was evaluated by the in vitro kinase assay.

The experimental method was summarized below:

The in vitro activity of TRKA G595R was measured using a HTRF kinase assay kit (Cisbio, No. 62TKOPEC) by detecting the phosphorylation level of the substrate in the kinase reaction. The reaction buffer contained the following components: the reaction buffer of the enzyme in the kit (1×), 5 mM $MgCl_2$, 1 mM DTT. The humanized recombined TRKA G595R protein (No. N16-12BG, purchased from Signal Chem Life Sciences) was diluted into 0.25 ng/kinase solution with the reaction buffer. The substrate reaction solution comprised 0.51 µM biotin-labeled tyrosine kinase substrate and 2.9 µM ATP, which was diluted with reaction buffer. The detection buffer comprised 0.15 ng/µL cage antibody labelled with Eu3+ and 31.875 nM XL665 labeled with streptavidin, which was diluted with reaction buffer.

The compound was dissolved into 100% DMSO and diluted to 1 mM or 100 µM, then diluted with DMSO in 4 times serial dilution to a minimum concentration of 61 or 6.1 nM, and each concentration point was further diluted 40 times with the reaction buffer.

4 µl of solution of the test compound and 2 µl of solution of TRKA G595R kinase were added to the 384 well plate (Corning No. 4512), mixed well and incubated at room temperature for 15 minutes. Then 4 µl of solution of substrate was added and the reaction mixture was incubated at room temperature for 60 minutes. 10 µl of detection buffer of the same volume as the reaction mixture was then added, the reaction mixture was mixed well and allowed to stand for 30 minutes at room temperature. The reaction process was monitored at the wavelength of 620 nm and 665 nm by Envision board reader (Perkin Elmer). The ratio of 665/620 was positively correlated with the phosphorylation level of the substrate, then TRKA G595R kinase activity was determined. In this experiment, the group without TRKA G595R kinase was used as the negative control (100% inhibition), the group with TRKA G595R but without the test compound was used as the positive control (0% inhibition). The inhibition percentage of the test compound on TRKA G595R activity can be calculated by the following formula:

Inhibition percentage=100−100*(signal value of the test compound under specific concentration−signal value of the negative control)/(signal value of the positive control−signal value of the negative control)

The $IC_{50}$ value of the test compound was calculated at 8 concentration points by use of XLfit (ID Business Solutions Ltd. UK) software through the following formula:

$$Y=\text{Bottom}+(\text{Top}-\text{Bottom})/(1+10^{((\log IC_{50}-X)*\text{slope factor})})$$

Of which Y is the inhibition percentage, X is the logarithm of the concentration of the compound to be tested, Bottom is the maximum inhibition percentage, Top is the minimum inhibition percentage, slope factor is the slope coefficient of the curve.

TRKA G667C Activity Inhibition Test:

The effect of the compounds of the invention on the activity of TRKA G667C was evaluated by the in vitro kinase assay.

The experimental methods were summarized below:

The in vitro activity of TRKA G667C was measured using a HTRF kinase assay kit (Cisbio, No. 62TKOPEC) by detecting the phosphorylation level of the substrate in the kinase reaction.

The reaction buffer contained the following components: reaction buffer of the enzyme in the kit (1×), 5 mM $MgCl_2$, 1 mM DTT. The humanized recombined TRKA G667C protein (No. N16-12 CG, Signal Chem Life Sciences) was diluted into 0.09 ng/µl kinase solution with the reaction buffer. The substrate reaction solution comprised 0.21 µM biotin-labeled tyrosine kinase substrate and 2.7 µM ATP, which was diluted with reaction buffer. The detection buffer comprised 0.1 ng/µL cage antibody labelled with Eu3+ and 13.125 nM XL665 labeled with streptavidin, which was diluted with reaction buffer.

The compound was dissolved into 100% DMSO and diluted to 200 µM, then diluted with DMSO in 4 times serial dilution to a minimum concentration of 12.2 nM, and each concentration point was further diluted 40 times with the reaction buffer.

4 µl of solution of the test compound and 2 µl of solution of TRKA G667C kinase were added to the 384 well plate (Corning No. 4512), mixed well and incubated at room temperature for 15 minutes. Then 4 µl of the solution of substrate was added and the reaction mixture was incubated at room temperature for 60 minutes. 10 µl of detection buffer of the same volume as the reaction mixture was then added. The reaction mixture was mixed well and allowed to stand for 30 minutes at room temperature. The reaction process was monitored at the wavelength of 620 nm and 665 nm by Envision board reader (Perkin Elmer). The ratio of 665/620 was positively correlated with the phosphorylation level of the substrate, then TRKA G667C kinase activity was determined.

In this experiment, the group without TRKA G667C kinase was used as the negative control (100% inhibition), the group with TRKA G667C kinase but without the test compound was used as the positive control (0% inhibition). The inhibition percentage of the test compound on TRKA G667C activity can be calculated by the following formula:

Inhibition percentage=100−100*(signal value of the test compound under specific concentration−signal value of negative control)/(signal value of positive control−signal value of negative control)

The $IC_{50}$ value of the compound was calculated at 8 concentration points by XLfit (ID Business Solutions Ltd. UK) software through the following formula:

$Y$=Bottom+(Top−Bottom)/(1+10^((log $IC_{50}$−$X$)*slope factor))

Of which Y is the inhibition percentage, X is the logarithm of the concentration of the compound to be tested, Bottom is the maximum inhibition percentage, Top is the minimum inhibition percentage, slope factor is the slope coefficient of the curve.

Determination of Median Effective Inhibition Concentration GI50 in KM12 Cells

The effect of the compounds of the invention on the proliferation of KM12 cells was evaluated by the luminescent cell viability test.

The experimental methods were summarized as follows:

CellTilter-Glo (CTG) detection kit was used. A unique and stable luciferase was used to detect ATP, an indicator of viable cell metabolism. The luminescence signal generated in the experiment was proportional to the number of viable cells in the culture medium, thus the proliferation of KM12 cells was detected.

KM12 cell (purchased from Shanghai Xinyu biological Co.) was cultured in IMDM complete medium (Thermo Fisher, 12440053) containing 10% FBS (GBICO, 10099-141) and 100 units/ml of penicillin streptomycin mixture (Thermofisher, 15140122). When the cell coverage rate in the culture container reached 80-90%, 0.25% trypsin (containing EDTA) (Thermofisher, 25200056) was used to digest and disperse the cells, then they were planted in a white 384 well plate (164610). To each well containing 1000 cells was added 27 μL IMDM complete medium. Then the 384 well plate was cultured overnight in an incubator containing 5% $CO_2$ at 37° C. The compound was dissolved into 100% DMSO and diluted to 1 mM, then diluted with DMSO in 4 times serial dilution to the lowest concentration of 0.061 μM. Each concentration point was further diluted 50 times with IMDM medium. If the $IC_{50}$ value of the compound was very low, the initial concentration of the compound can be reduced. 3 μl Diluted compound was added into each well, centrifuged and mixed well gently. The medium without cells was used as negative control (100% inhibition), and the group with 0.2% DMSO was used as positive control (0% inhibition).

The 384 well plate was placed in the incubator at 37° C. and 5% $CO_2$ for further incubation. After 96 hours, the plate was taken out and placed at room temperature for 30 minutes. The CTG reagent was also taken out and equilibrated to room temperature. 15 μl of CTG reagent was added to each well and shaken gently for 5 minutes on a shaker to ensure sufficient cell lysis. After 10 minutes of standing, the cold light signal was stable. Then the cold light signal was read by Envision (Perkin Elmer). In addition, to correct the number of cells, To control was set at the same time, including the blank control containing only culture medium and the control with added cells. The difference between the two was set as $T_0$ control, which was obtained by adding CTG reagent before adding the compounds.

The percentage of inhibition of KM12 cell proliferation by the compounds can be calculated by the following formula:

Inhibition percentage=100−100*{[(Signal$_{compound}$−Signal$_{negative\ control}$)−$T_{0control}$]/[(Signal$_{positive\ control}$−Signal$_{negative\ control}$)−$T_{0control}$]}

The $IC_{50}$ values of compounds were calculated by XLfit (ID Business Solutions Ltd., UK) software at 8 concentration points through the following formula:

$Y$=Bottom+(Top−Bottom)/(1+10^((Log IC50−$X$)* slope factor))

Of which, Y is the inhibition percentage, Bottom is the bottom plateau of the curve (the bottom platform value of S curve), Top is the top plateau of the curve (the top platform value of S curve), X is the logarithm of the concentration of the compound to be measured.

Biological Experiment Results were Shown in Table I

| Number of Compound | TRKA $IC_{50}$ (nM) | TRKA G595R $IC_{50}$ (nM) | TRKA G667C $IC_{50}$ (nM) | KM12 cell GI50 (nM) |
|---|---|---|---|---|
| 1 | 0.24 | 0.26 | 1.63 | 0.43 |
| 2 | 0.97 | 12.2 | 16.27 | 3.12 |
| 3 | 1.46 | 10.19 | ND | 33.66 |
| 4 | 1.08 | 1.4 | ND | 2.26 |

Note:
ND = not determined.

From the above experimental results, it can be seen that compounds of the examples in the present invention can effectively inhibit the activity of TRKA and TRKA kinase with G595R and G667C mutations, and can be used to treat a variety of cancers caused by NTRK gene fusion, such as glioma, hepatobiliary carcinoma, papillary thyroid carcinoma, colon cancer, non-small cell lung cancer, head and neck squamous cell carcinoma, pancreatic carcinoma, sarcoma and melanoma (Khotskaya, Y. B. et al. *Pharmacology & Therapeutics*, 2017, 173, 58-66). Some compounds can also inhibit the proliferation of KM12 colon cancer cells. It has strong inhibitory effect on colon cancer caused by NTRK gene fusion.

For those skilled in the art, it is obvious that the present disclosure is not limited to the examples described above and can be implemented in other specific forms without departing from the substantive characteristics of the present disclosure. Therefore, it is expected that these embodiments are illustrative and non-restrictive in all aspects, and reference should be made to the additional claims rather than the above-mentioned embodiments, and thus all changes within the equivalent and scope of the claims are included therein.

The invention claimed is:

1. A compound as shown in formula I, or an isomer, prodrug, solvate, stable isotopic derivative or pharmaceutically acceptable salt thereof:

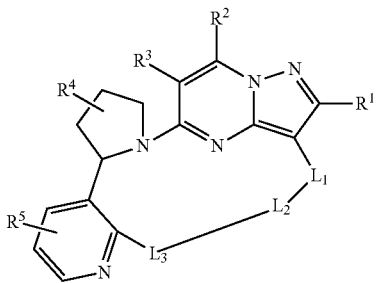

wherein:

L₁ is selected from —NR⁶C(O)—, —NR⁶CON(R⁷)—, —NR⁶S(O)ₘ— and —NR⁶S(O)ₘN(R⁷)—, of which NR⁶ is connected with the nitrogen-containing heteroaryl substituted by R¹, R², R³;

L₂ is selected from C1-C8 alkylene, C2-C8 alkenylene, C2-C8 alkynylene and C3-C8 cyclylene, wherein the alkylene, alkenylene, alkynylene and cyclylene can be optionally substituted by one or more G1;

L₃ is selected from a single bond, —O— and —N(Rˣ);

R¹, R², and R³ are each independently selected from hydrogen, halogen, cyano, C1-C8 alkyl, C3-C8 cyclyl, 3-8 membered heterocyclyl, aryl, heteroaryl, formyl, —NR⁸R⁹, —C(O)R¹⁰, carboxyl, alkenyl, alkynyl, —OR¹⁰, —OC(O)NR⁸R⁹, —C(O)OR¹⁰, —C(O)NR⁸R⁹, —NR¹¹C(O)R¹⁰, —NR¹¹C(O)NR⁸R⁹, —S(O)mR¹⁰, —N¹¹S(O)mR¹⁰, —SR¹⁰, —S(O)mNR⁸R⁹ and —NR¹¹S(O)mNR⁸R⁹, wherein the alkyl, cyclyl, heterocyclyl, aryl or heteroaryl are optionally substituted by one or more substituents selected from halogen, cyano, C1-C8 alkyl, C3-C8 cyclyl, 3-8 membered heterocyclyl, —OR¹², —NR¹³R¹⁴, —OC(O)NR¹³R¹⁴, —C(O)OR¹², —C(O)R¹², —C(O)NR¹³R¹⁴, —NR¹⁵C(O)R¹², —NR¹⁵C(O)NR¹³R¹⁴, —S(O)mR¹², —NR¹⁵S(O)mR¹², —SR¹², —S(O)mNR¹³R¹⁴ and —NR¹⁵S(O)mNR¹³R¹⁴;

R⁴ is selected from hydrogen, halogen, cyano, C1-C8 alkyl, C3-C8 cyclyl, 3-8 membered heterocyclyl, aryl, heteroaryl, formyl, —C(O)R¹⁰, carboxyl, alkenyl, alkynyl, —OR¹⁰, —NR⁸R⁹, —OC(O)NR⁸R⁹, —C(O)OR¹⁰, —C(O)NR⁸R⁹, —NR⁸C(O)R¹⁰, —NR¹⁰C(O)NR⁸R⁹, —S(O)mR¹⁰, —NR⁸S(O)mR¹⁰, —SR¹⁰, —S(O)mNR⁸R⁹, and —NR¹⁰S(O)mNR⁸R⁹;

R⁵ is selected from hydrogen, halogen, cyano, C1-C8 alkyl, C3-C8 cyclyl, 3-8 membered heterocyclyl, aryl, heteroaryl, formyl, —C(O)R¹⁰, carboxyl, alkenyl, alkynyl, —OR¹⁰, —NR⁸R⁹, —OC(O)NR⁸R⁹, —C(O)OR¹⁰, —C(O)NR⁸R⁹, —NR⁸C(O)R¹⁰, —NR¹⁰C(O)NR⁸R⁹, —S(O)mR¹⁰, —NR⁸S(O)mR¹⁰, —SR¹⁰, —S(O)mNR⁸R⁹ and —NR¹⁰S(O)mNR⁸R⁹;

R⁶, R⁷, and Rˣ are each independently selected from hydrogen, C1-C8 alkyl, C1-C8 haloalkyl, heteroalkyl, C3-C8 cyclyl, 3-8 membered monocyclic heterocyclyl, monocyclic heteroaryl, monocyclic aryl, alkenyl and alkynyl;

G1 is selected from halogen, cyano, C1-C8 alkyl, C3-C8 cyclyl, 3-8 membered heterocyclyl, aryl, heteroaryl, formyl, —NR⁸R⁹, —C(O)R¹⁰, carboxyl, alkenyl, alkynyl, —OR¹⁰, —OC(O)NR⁸R⁹, —C(O)OR¹⁰, —C(O)NR⁸R⁹, —NR¹¹C(O)R¹⁰, —NR¹¹C(O)NR⁸R⁹, —S(O)mR¹⁰, —N¹¹S(O)mR¹⁰, —S(O)mNR⁸R⁹ and —NR¹¹S(O)mNR⁸R⁹; when two G1s are connected to the same carbon atom or two adjacent carbon atoms, the two G1s can form a 3-8 membered cyclyl together with the carbon atom(s) connected with them;

R⁸, R⁹, R¹⁰, R¹¹, R¹², R¹³, R¹⁴, R¹⁵ and R¹⁶ are each independently selected from the group consisting of hydrogen, C1-C8 alkyl, C1-C8 haloalkyl, heteroalkyl, C3-C8 cyclyl, 3-8 membered monocyclic heterocyclyl, monocyclic heteroaryl, monocyclic aryl, alkenyl and alkynyl, wherein R⁸ and R⁹, and R¹³ and R¹⁴ may form a 3-7 membered heterocyclyl;

and m is 1 or 2;

wherein the following compounds (1) to (7) are excluded:

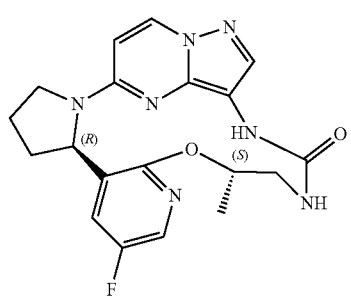

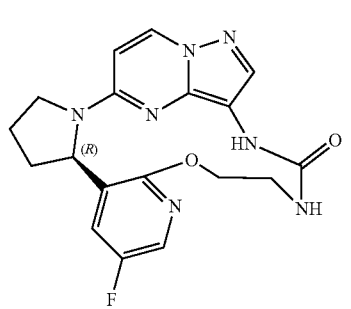

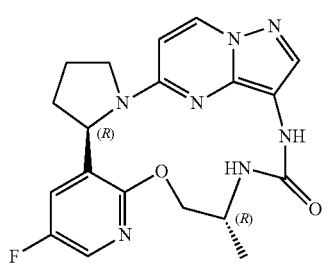

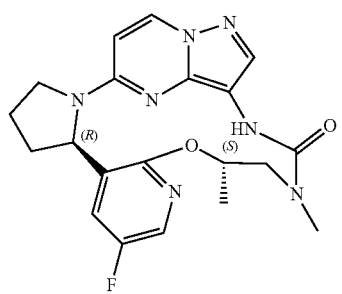

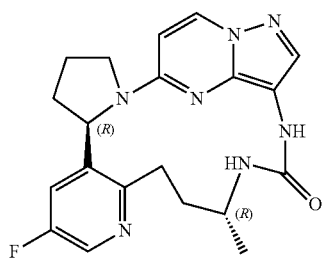

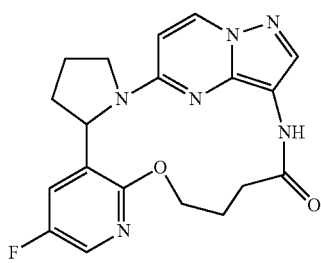
(6)

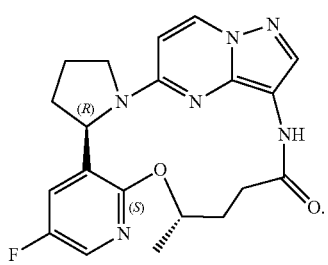
(7)

2. The compound according to claim 1, or an isomer, prodrug, solvate, stable isotopic derivative or pharmaceutically acceptable salt thereof, wherein:
$L_1$ is selected from —NR$^6$C(O)—, —NR$^6$CON(R$^7$)—, —NR$^6$S(O)$_m$— and —NR$^6$S(O)$_m$N(R$^7$)—, of which NR$^6$ is connected with the nitrogen-containing heteroaryl substituted by R$^1$, R$^2$, R$^3$;
$L_2$ is selected from C1-C6 alkylene, C2-C6 alkenylene, C2-C6 alkynylene and C3-C6 cyclylene, wherein the alkylene, alkenylene, alkynylene and cyclylene can be optionally substituted by one or more G1;
$L_3$ is selected from a single bond and —O—;
R$^1$, R$^2$, and R$^3$ are each independently selected from hydrogen, halogen, C1-C6 alkyl, C3-C6 cyclyl, 3-6 membered heterocyclyl, aryl and heteroaryl, wherein the alkyl, cyclyl, heterocyclyl, aryl or heteroaryl are optionally substituted by one or more substituents selected from halogen, cyano, C1-C6 alkyl, C3-C6 cyclyl and 3-6 membered heterocyclyl;
R$^4$ is selected from hydrogen, halogen, —NR$^8$R$^9$, and —OR$^{10}$,
R$^5$ is selected from hydrogen, halogen, C1-C6 alkyl and C3-C6 cyclyl;
R$^6$ and R$^7$ are each independently selected from hydrogen, C1-C6 alkyl, and C1-C6 haloalkyl;
G1 is selected from halogen, C1-C6 alkyl, and —NR$^8$R$^9$, —OR$^{10}$, wherein the alkyl is optionally substituted by one or more substituents selected from halogen, —NR$^{11}$R$^{12}$, and —OR$^{16}$;
R$^8$, R$^9$, R$^{10}$, R$^{11}$, R$^{12}$ and R$^{16}$ are each independently selected from hydrogen, C1-C6 alkyl and C1-C6 haloalkyl;
and m is 1 or 2;
wherein the following compounds (1) to (7) are excluded:

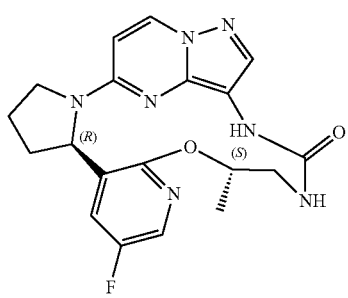
(1)

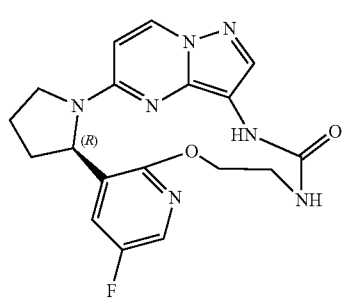
(2)

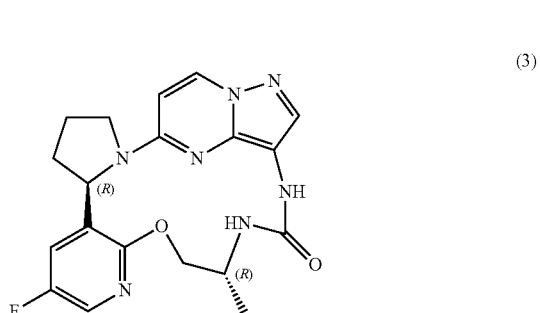
(3)

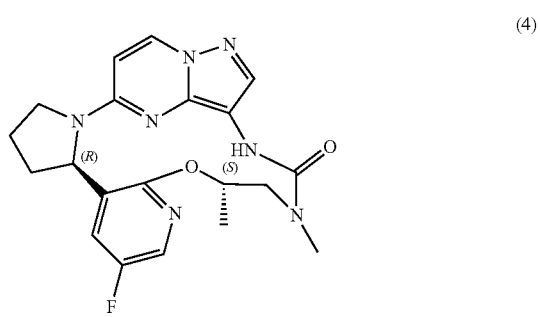
(4)

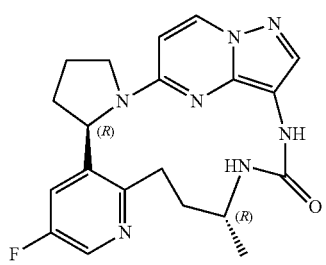
(5)

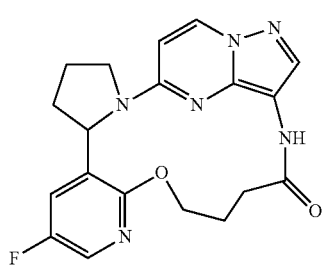
(6)

-continued

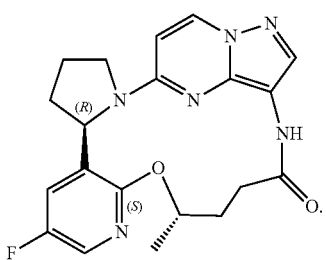
(7)

3. The compound according to claim 1, or an isomer, prodrug, solvate, stable isotopic derivative or pharmaceutically acceptable salt thereof, wherein:

$L_1$ is selected from —NR$^6$C(O)— and —NR$^6$CON(R$^7$)—, wherein NR$^6$ is connected with the nitrogen-containing heteroaryl substituted by R$^1$, R$^2$, and R$^3$;

$L_2$ is selected from C1-C6 alkylene, C2-C6 alkenylene, C2-C6 alkynylene and C3-C6 cyclylene, wherein the alkylene, alkenylene, alkynylene and cyclylene can be optionally substituted by one or more G1;

$L_3$ is selected from a single bond and —O—;

R$^1$, R$^2$, and R$^3$ are each independently selected from hydrogen, halogen, C1-C4 alkyl, C4-C6 cyclyl, and 4-6 membered heterocyclyl, wherein the alkyl, cyclyl and heterocyclyl are optionally substituted by one or more substituents selected from halogen;

R$^4$ is selected from hydrogen, halogen, —NR$^8$R$^9$, and —OR$^{10}$,

R$^5$ is selected from hydrogen, halogen, C1-C6 alkyl and C3-C6 cyclyl;

R$^6$ and R$^7$ are each independently selected from hydrogen, C1-C6 alkyl, and C1-C6 haloalkyl;

G1 is selected from halogen, C1-C6 alkyl, —NR$^8$R$^9$, and —OR$^{10}$, wherein the alkyl is optionally substituted by one or more substituents selected from halogen, —NR$^{11}$R$^{12}$, and —OR$^{16}$; and R$^8$, R$^9$, R$^{10}$, R$^{11}$, R$^{12}$ and R$^{16}$ are each independently selected from hydrogen, C1-C6 alkyl and C1-C6 haloalkyl;

wherein the following compounds (1) to (7) are excluded:

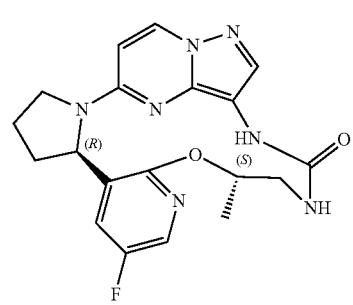
(1)

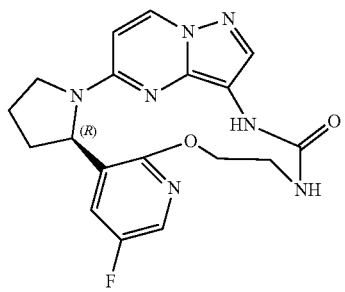
(2)

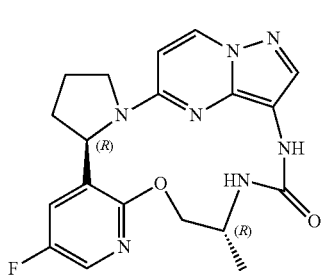
(3)

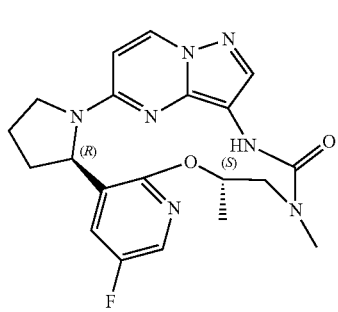
(4)

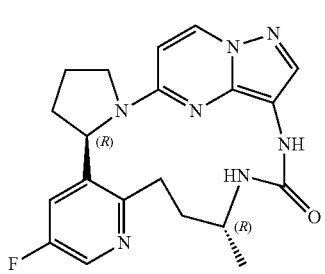
(5)

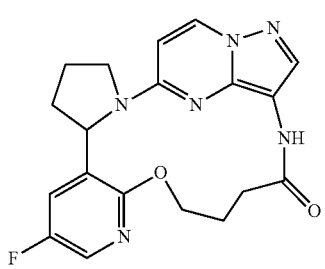
(6)

-continued (7)
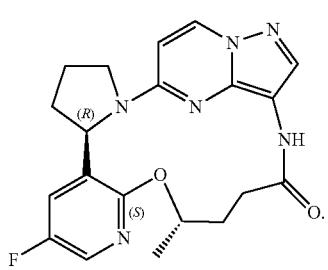

-continued (2)
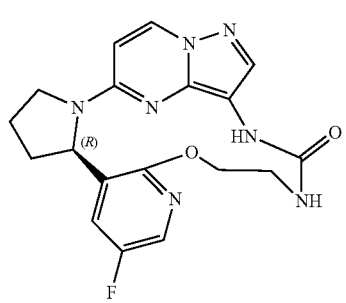

4. The compound according to claim 1, or an isomer, prodrug, solvate, stable isotopic derivative or pharmaceutically acceptable salt thereof,
wherein:
$L_1$ is —NR$^6$CON(R$^7$)—, of which NR$^6$ is connected with the nitrogen-containing heteroaryl substituted by R$^1$, R$^2$, and R$^3$;
$L_2$ is selected from C1-C4 alkylene, C2-C4 alkenylene, C2-C4 alkynylene and C3-C4 cyclylene, wherein the alkylene, alkenylene, alkynylene and cyclylene can be optionally substituted by one or more G1;
$L_3$ is selected from a single bond and —O—;
R$^1$, R$^2$, and R$^3$ are each independently selected from hydrogen, halogen and C1-C4 alkyl, wherein the alkyl is optionally substituted by one or more substituents selected from halogen;
R$^4$ is selected from hydrogen, halogen, —NR$^8$R$^9$, and —OR$^{10}$,
R$^5$ is selected from hydrogen, halogen, C1-C6 alkyl and C3-C6 cyclyl;
R$^6$ and R$^7$ are each independently selected from hydrogen, C1-C6 alkyl, and C1-C6 haloalkyl;
G1 is selected from halogen, C1-C6 alkyl, and —NR$^8$R$^9$, —OR$^{10}$, wherein the alkyl is optionally substituted by one or more substituents selected from halogen, —NR$^{11}$R$^{12}$, and —OR$^{16}$; and
R$^8$, R$^9$, R$^{10}$, R$^{11}$, R$^{12}$ and R$^{16}$ are each independently selected from the group consisting of hydrogen, C1-C6 alkyl and C1-C6 haloalkyl;
wherein the following compounds (1) to (5) are excluded:

(1)
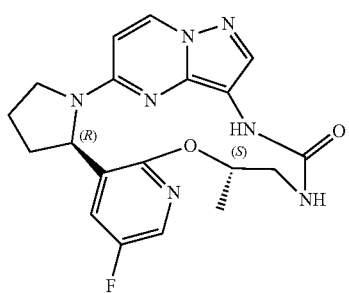

(3)
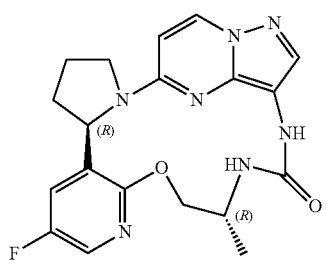

(4)
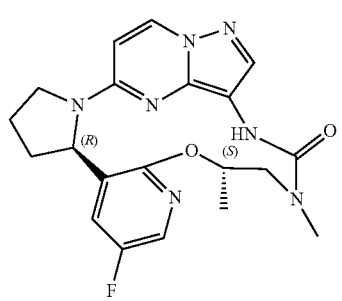

(5)
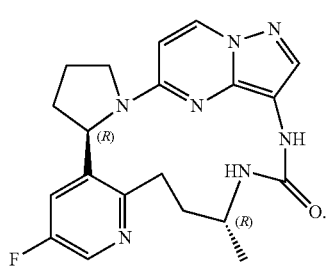

5. The compound according to claim 1, or an isomer, prodrug, solvate, stable isotopic derivative or pharmaceutically acceptable salt thereof,
wherein:
$L_1$ is NR$^6$CON(R$^7$)—, of which NR$^6$ is connected with the nitrogen-containing heteroaryl substituted by R$^1$, R$^2$, and R$^3$;
$L_2$ is selected from C1-C4 alkylene and C2-C4 alkenylene, wherein the alkylene and alkenylene can be optionally substituted by one or more G1;
$L_3$ is selected from a single bond and —O—;
R$^1$, R$^2$, and R$^3$ are each independently selected from hydrogen, halogen and C1-C4 alkyl, wherein the alkyl is optionally substituted by one or more substituents selected from halogen;
R$^4$ is selected from hydrogen, halogen, —NR$^8$R$^9$, and —OR$^{10}$;
R$^5$ is selected from hydrogen, halogen, C1-C4 alkyl and C3-C6 cyclyl;
R$^6$ and R$^7$ are each independently selected from hydrogen, C1-C4 alkyl, and C1-C4 haloalkyl;

G1 is selected from halogen, C1-C4 alkyl, —NR⁸R⁹, and —OR¹⁰, wherein the alkyl is optionally substituted by one or more substituents selected from halogen, —NR¹¹R¹², and —OR¹⁶; and R⁸, R⁹, R¹⁰, R¹¹, R¹² and R¹⁶ are each independently selected from hydrogen, C1-C4 alkyl, and C1-C4 haloalkyl;

wherein the following compounds (1) to (5) are excluded:

(1)
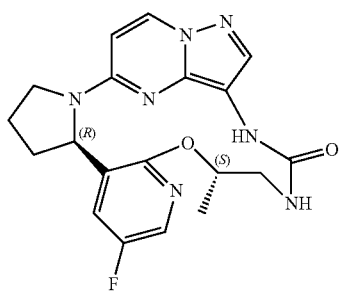

(2)
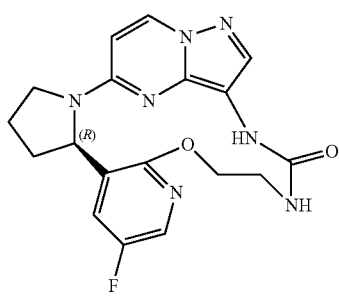

(3)
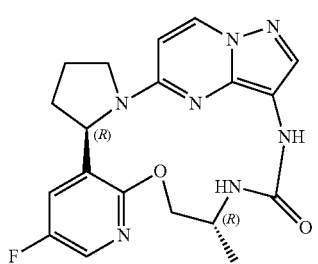

(4)
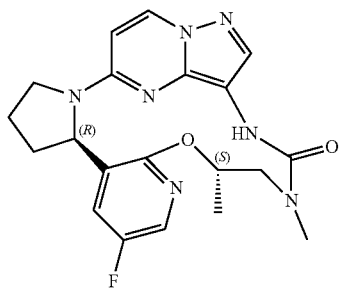

(5)
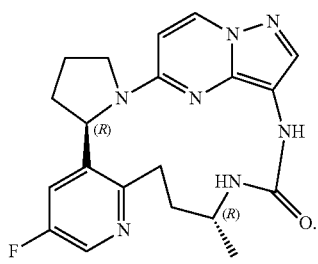

6. The compound according to claim 1, or an isomer, prodrug, solvate, stable isotopic derivative or pharmaceutically acceptable salt thereof, wherein:

L₁ is selected from —NR⁶CON(R⁷)—, of which NR⁶ is connected with the nitrogen-containing heteroaryl substituted by R¹, R², and R³;

L₂ is selected from C1-C4 alkylene, wherein the alkylene can be optionally substituted by one or more G1;

L₃ is —O—;

R¹, R², and R³ are each independently selected from hydrogen, halogen and C1-C4 alkyl, wherein the alkyl is optionally substituted by one or more halogen;

R⁴ is selected from hydrogen, halogen, —NR⁸R⁹, and —OR¹⁰;

R⁵ is selected from hydrogen, halogen and C1-C4 alkyl;

R⁶ and R⁷ are each independently selected from hydrogen, C1-C4 alkyl, and C1-C4 haloalkyl;

G1 is selected from halogen, C1-C4 alkyl, —NR⁸R⁹, and —OR¹⁰, wherein the alkyl is optionally substituted by one or more substituents selected from halogen, —NR¹¹R¹², and —OR¹⁶; and R⁸, R⁹, R¹⁰, R¹¹, R¹² and R¹⁶ are each independently selected from hydrogen, C1-C4 alkyl and C1-C4 haloalkyl;

wherein the following compounds (1) to (4) are excluded:

(1)
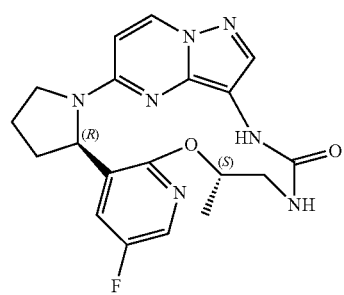

(2)
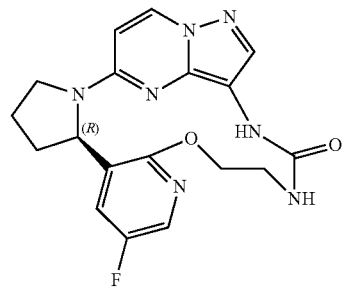

(3)
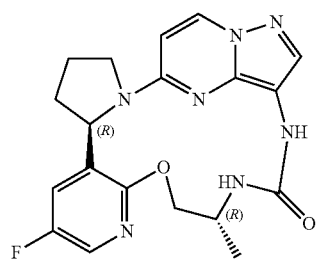

-continued (4)

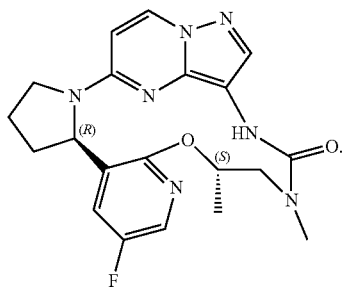

7. The compound according to claim 1, or an isomer, prodrug, solvate, stable isotopic derivative or pharmaceutically acceptable salt thereof,
wherein:
L₁ is selected from NR⁶CON(R⁷)—, of which NR⁶ is connected with the nitrogen-containing heteroaryl substituted by R¹, R², and R³;
L₂ is Selected from C1-C4 alkylene, wherein the alkylene can be optionally substituted by one or more G1;
L₃ is —O—;
R¹, R², and R³ are each independently selected from hydrogen and halogen;
R⁴ is selected from hydrogen and halogen;
R⁵ is selected from hydrogen, halogen and C1-C4 alkyl, and is located at the para position of L₃;
R⁶ and R⁷ are each independently selected from hydrogen and C1-C4 alkyl;
G1 is selected from halogen and C1-C4 alkyl, wherein the alkyl is optionally substituted by one or more substituents selected from halogen, —NR¹¹R¹², and —OR¹⁶; and
R¹¹, R¹² and R¹⁶ are each independently selected from hydrogen, C1-C4 alkyl and C1-C4 haloalkyl;
wherein the following compounds (1) to (4) are excluded:

(1)

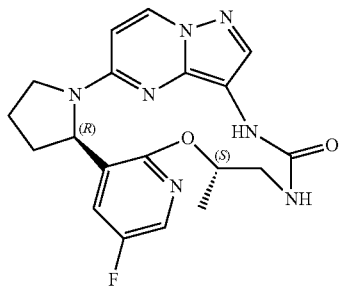

(2)

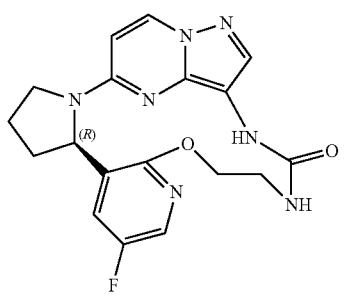

-continued (3)

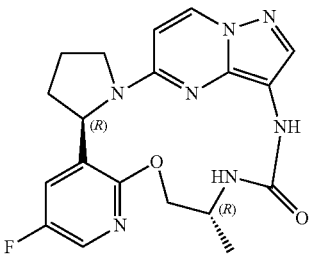

(4)

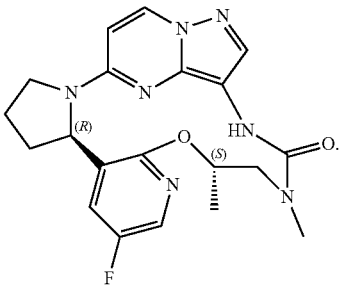

8. The compound according to claim 1, or an isomer, prodrug, solvate, stable isotopic derivative or pharmaceutically acceptable salt thereof, characterized in that the compounds are selected from:

1

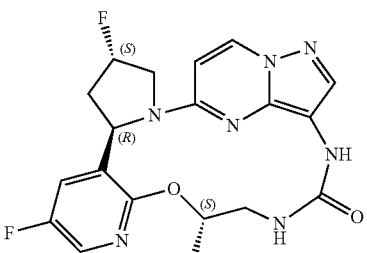

2

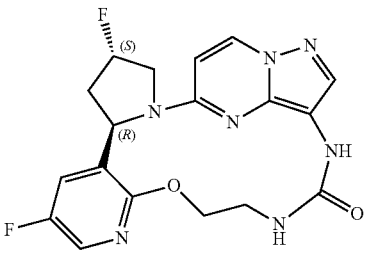

3

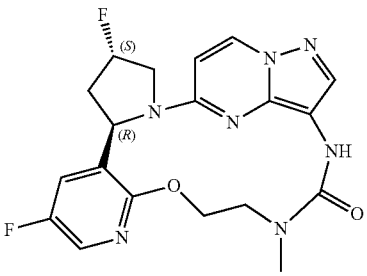

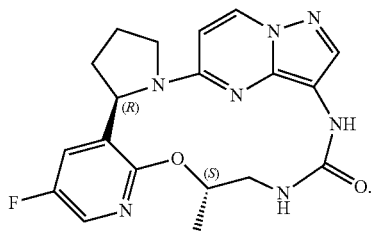

9. A pharmaceutical composition comprising the compound according to claim 1, prodrug, solvate, stable isotopic derivative or pharmaceutically acceptable salt thereof, and a pharmaceutically acceptable carrier, diluent, or excipient.

10. A method of treating a TRK mediated disease, wherein the TRK mediated disease is selected from a hematological malignancy, lung cancer, breast cancer, ovarian cancer, prostate cancer, pancreatic cancer, and a glioma, the method comprising administering to a subject in need thereof an effective amount of a compound according to claim 1 or an isomer, prodrug, solvate, stable isotopic derivative or pharmaceutically acceptable salt thereof.

* * * * *